(12) United States Patent
Jiang et al.

(10) Patent No.: US 7,067,244 B2
(45) Date of Patent: Jun. 27, 2006

(54) RAPID TRIGLYCERIDE ASSAY FOR USE IN PULP PITCH CONTROL

(76) Inventors: Chengliang Jiang, 2173 Soque River Dr., Duluth, GA (US) 30097; Xiang H. Wang, 12630 Oxfordshire Ct., Alpharetta, GA (US) 30005; Robin M. Yezzi, 2512 Haddenham La., Smyrna, GA (US) 30082; James G. Tausche, 1001 Defoors Mill Dr., Atlanta, GA (US) 30318

( * ) Notice: Subject to any disclaimer, the term of this patent is extended or adjusted under 35 U.S.C. 154(b) by 437 days.

(21) Appl. No.: 10/126,173

(22) Filed: Apr. 19, 2002

(65) Prior Publication Data

US 2003/0046984 A1    Mar. 13, 2003

Related U.S. Application Data

(60) Provisional application No. 60/285,259, filed on Apr. 20, 2001.

(51) Int. Cl.
- *C12Q 1/00* (2006.01)
- *A61K 35/78* (2006.01)
- *D01C 3/20* (2006.01)

(52) U.S. Cl. ............................ 435/4; 424/769; 162/71; 162/72; 162/91

(58) Field of Classification Search ...................... None
See application file for complete search history.

(56) References Cited

U.S. PATENT DOCUMENTS

| | | | |
|---|---|---|---|
| 4,045,297 A | 8/1977 | Weeks et al. | |
| 4,142,938 A | 3/1979 | Stavropoulos et al. | |
| 4,223,090 A | 9/1980 | Mazza | |
| 4,241,178 A | 12/1980 | Esders et al. | |
| 4,245,041 A | 1/1981 | Denney | |
| 4,259,440 A | 3/1981 | Gupta et al. | |
| 4,273,870 A | 6/1981 | Mollering et al. | |
| 4,309,502 A | 1/1982 | Lauderdale | |
| 4,394,445 A | 7/1983 | Nix et al. | |
| 4,636,465 A | 1/1987 | Itoh et al. | |
| 4,713,165 A | 12/1987 | Conover et al. | |
| 4,923,796 A | 5/1990 | Deneke et al. | |
| 5,110,724 A | 5/1992 | Hewett | |
| 5,176,796 A | 1/1993 | Irie et al. | |
| 5,179,021 A | 1/1993 | du Manoir et al. | |
| 5,221,615 A | 6/1993 | Modrovich et al. | |
| 5,256,252 A | 10/1993 | Sarkar et al. | |
| 5,278,046 A | 1/1994 | Johnson et al. | |
| 5,597,532 A | 1/1997 | Connolly | |
| 5,667,634 A * | 9/1997 | Fujita et al. | ................... 162/72 |
| 5,698,667 A | 12/1997 | Speaks et al. | |
| 5,989,392 A | 11/1999 | Tang et al. | |
| 5,989,409 A | 11/1999 | Kurnik et al. | |
| 6,134,952 A | 10/2000 | Garver et al. | |
| 6,242,245 B1 * | 6/2001 | Amann et al. | ............... 435/277 |
| 6,471,826 B1 * | 10/2002 | Glover et al. | ................ 162/158 |

OTHER PUBLICATIONS del Rio, et al., "Analysis of Pitch Deposits Produced in Kraft Pulp Mills Using a Totally Chlorine Free Bleaching Sequence," *J. Chromatogr A*, 874(2):235-45 (Apr. 7, 2000) (Abstract Only).

Maister, "Growing Market for Industrial Enzymes" p. 16B, Atlanta Business Chronicle (Mar. 16-22, 2001).

Sigma Diagnostics Inc., Triglyceride (GPO-Trinder) Procedure No. 337 (1989, 1998 Sigma-Aldrich Co.).

Sigma Diagnostics Inc., Triglyceride (INT) Procedure No. 336 (1989, 1998 Sigma-Aldrich Co.).

"Lipids and Lipoproteins" pp. 496-506.

* cited by examiner

*Primary Examiner*—Christopher R. Tate
(74) *Attorney, Agent, or Firm*—Pabst Patent Group LLP

(57) ABSTRACT

Enzymatic methods are provided for determining the surface triglycerides content in a sample of wood pulp. The methods preferably comprise reacting triglycerides which are present on the surface of the wood pulp fibers in the sample in the presence of a lipase to form glycerol and fatty acids, and then determining the difference between the amount of free glycerol present in the sample and the amount of glycerol formed from said triglycerides. The method is useful as a quick, portable, accurate, and low cost assay for assessing the amount of triglycerides present at various sample points in pulp and paper mills, which advantageously serves as a diagnostic tool for use in controlling the undesirable deposition of pitch during the papermaking process.

60 Claims, 12 Drawing Sheets

Effect of peroxide on the assay for pulp without residual hydrogen peroxide or hydrosulfite (PC-A and PC-B)

Effect of hydrosulfite concentration on assay for pulp without residual hydrogen peroxide or hydrosulfite (PC-A and PC-B).

Effect of peroxide on a 100 ppm triolein sample with 1000 ppm of hydrosulfite using assay for pulp containing hydrogen peroxide and hydrosulfite (PC-Y and PC-Z).

RAPID TRIGLYCERIDE ASSAY FOR USE IN PULP PITCH CONTROL

CROSS-REFERENCE TO RELATED APPLICATIONS

Priority is claimed under 35 U.S.C. § 119 to U.S. provisional application Ser. No. 60/285,259, filed Apr. 20, 2001.

FIELD OF THE INVENTION

The methods, compositions, and kits described herein are generally in the field of diagnostic tools and methods for use in controlling pitch in pulp and paper mill processes.

BACKGROUND OF THE INVENTION

Minimizing or preventing the deposit of pitch in pulp and paper making processes is critical to minimizing equipment fouling and down time, maximizing production efficiency, and improving product quality. Pitch is composed of low molecular weight olephilic materials (primarily triglycerides, fatty acids, terpenes, resin acids and esters), which are released from wood fibers during chemical and mechanical pulping processes. This resinous substance usually precipitates as calcium and magnesium salts, causing problems with the wet end components of paper machines.

Known methods for pitch control include cationic fixation with alum or cationic polymers, dispersion with surfactants, absorption with talc, and chelation of heavy metals. Enzymatic methods also are known. For example, U.S. Pat. No. 5,176,796 to Irie, et al. discloses adding acylglycerol lipase to mechanical pulp paperstock or reuse water; U.S. Pat. No. 5,256,252 to Sarkar et al. discloses adding a lipase and a cationic polymer to a papermaking cellulosic slurry; and U.S. Pat. No. 5,667,634 to Fujita et al. discloses adding a water-soluble polyelectrolyte to increase the hydrolysis rate of esters in the presence of a lipase.

Effectively employing these and other pitch control methods, however, requires an accurate assessment of the quantity of depositable pitch present in the pulp and process waters throughout several points in the papermaking process. Standard diagnostic techniques for measuring pitch include a test to measure the total organic extractive content of the pulp. Unfortunately, known methods of triglyceride analysis of pulp take between about 8 and 24 hours to complete one set of samples. Therefore, the test results are useful only for post evaluation of the process system; they do not provide an assessment of the current state of the process, and yield unreliable and unfocused results. Accordingly, use of analytical methods to accurately apply pitch control measures is quite limited, as the dynamic nature of the pitch level in a continuous papermaking process requires a timely response by the pitch control measures. It would be highly advantageous to have a method that analyzes the triglyceride content of the pulp quickly and accurately so that process parameters can be adjusted to timely and accurately prevent pitch deposition problems.

One current method of triglyceride analysis is based on the analysis of fatty acids produced by the reaction of triglyceride hydrolysis in the presence of lipase:

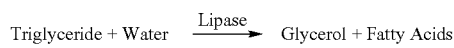

Triglyceride + Water →(Lipase) Glycerol + Fatty Acids

Briefly, the method steps include (1) analyzing the fatty acid content of a first pulp sample that has not been treated with enzyme using an extraction, evaporation, and titration procedure; (2) calculating the percent of organic acid as oleic acid for the first sample; (3) treating a second pulp sample with a high dose of enzyme under conditions to ensure complete conversion of triglyceride to fatty acids and glycerol; (4) analyzing the fatty acid content of the enzyme-treated second pulp sample using the extraction, evaporation, and titration procedure; and (5) comparing the difference of organic acid in the first sample and the second sample. The triglyceride content is determined by the difference of fatty acid content before and after lipase treatment of the pulp sample, multiplied by a conversion factor. The conversion factor is the ratio of the molecular weight of the triglycerides to the molecular weight of the fatty acids. It is assumed that at high lipase dosage, the triglycerides are converted entirely to fatty acids and glycerol. No side reactions occur.

The extensive extraction, evaporation, and titration procedures required to assess fatty acid content are time consuming and labor intensive. For example, the fatty acids in the pulp sample are extracted into a hexane layer and aliquots of the hexane layer then are evaporated, leaving an organic residual that subsequently is dissolved into an aqueous isopropanol solution, which is then titrated with potassium hydroxide solutions using thymol blue as a pH indicator.

Another method also involves an extensive solvent extraction step followed by a high cost instrumental analysis step, involving high performance liquid chromatography (HPLC), thin layer chromatography (TLC), or gas chromatography (GC). These extraction-based methods typically take between about 8 and 24 hours to complete, require the use of potentially dangerous volatile organic compounds or toxic solvents, and are very labor intensive. The instrumental analysis is not portable for on site analysis, and the results often are inaccurate or irreproducible. It would be advantageous to have an accurate test method that does not require the extraction step, so that the pulp could be tested directly and rapidly. Such a test preferably would be portable, fast and easy to use, without high cost instrumental analysis. It would be beneficial if the method also minimized or eliminated the tester's potential exposure to volatile organic compounds or toxic solvents required by the extraction-based methods.

A further disadvantage of known methods is that pitch deposition does not correlate directly with the total organic extractive content of the pulp. Rather it is the pitch on the surface of the pulp fibers or in the suspension, i.e. the depositable pitch, that is the greatest concern in pitch deposition. Total pitch consists of pitch located on the surface of the fibers and pitch trapped within the pulp fibers. The pitch trapped within the fibers generally does not contribute to the pitch deposition problem, as it remains intact within the fibers and does not have a chance to react. The extraction-based analytical methods described above give the content of the total organic extractive chemicals in the pulp sample, which has no close correlation with the pitch deposition problems. Therefore, a test method providing results that directly correlate to pitch depositions problems would be highly beneficial.

It would be desirable to provide methods, devices, and kits for accurately and rapidly determining the depositable triglyceride content of a pulp sample, particularly for use in a continuous papermaking process. It would also be desirable to provide methods for enhancing the effectiveness of pitch control measures in a papermaking process based on such determinations. It would further be desirable to provide methods for measuring the surface triglycerides in wood pulp, wherein the test is portable, fast and easy to use without high cost instrumental analysis, and minimizes or eliminates the tester's potential exposure to volatile organic compounds or toxic solvents required by extraction-based total organic content diagnostic assays.

SUMMARY OF THE INVENTION

Enzymatic methods are provided for determining the depositable triglyceride content in a suspension of wood pulp. The methods are useful for rapidly assessing the amount of triglycerides present at various sample points in pulp and paper mills, which advantageously serves as a diagnostic tool for use in controlling the undesirable deposition of pitch during the pulping and paper making process. The methods advantageously can be done at low cost using portable equipment, if desired.

The method for determining the depositable triglycerides content in a wood pulp sample comprises (1) reacting the depositable triglycerides in a wood pulp sample in the presence of a lipolytic enzyme, preferably a lipase, to form glycerol and fatty acids, and then (2) determining the difference between the amount of glycerol or fatty acid present in the wood pulp sample before and after treatment with the lipolytic enzyme. In preferred embodiments, the second step involves (a) forming a measurable species from one or more reactions, in which the glycerol or fatty acids present in the wood pulp sample is a reactant, and then (b) obtaining a quantitative measurement of the measurable species present in the sample before and after lipase treatment.

The quantitative measurement can be obtained from a test measuring a property such as concentration of an electrochemical species, spectrometric characteristics, or chromatographic characteristics. In one of the more preferred embodiments, the measurable species is a colored substrate and the quantitative measurement is obtained spectrophotometrically.

The method for determining the depositable triglycerides content can be conducted in a batch process (e.g., where samples are collected periodically and the test is conducted offline). Alternatively, the method for determining the depositable triglycerides content can be conducted in a continuous or semi-continuous process (e.g., online sampling/analysis).

A variety of reaction sequences can be used to convert the glycerol or fatty acids to an easily quantifiable, measurable species. Glycerol detection is preferred for its low cost, portability, accuracy, and short assay time.

In preferred embodiments, the glycerol is enzymatically reacted in a reaction sequence that produces the measurable species. The glycerol can be phosphorylated, for example to produce glycerol-1-phosphate or glycerol-3-phosphate. In a preferred embodiment, glycerol, glycerol-1-phosphate or glycerol-3-phosphate is then enzymatically oxidized with an electron acceptor.

Preferred examples of electron acceptors include oxygen ($O_2$), nicotinamide adenine dinucleotide ($NAD^+$), and nicotinamide adenine dinucleotide phosphate ($NADP^+$). In one embodiment, glycerol-1-phosphate or glycerol-3-phosphate can be reacted with oxygen ($O_2$) to form dihydroxyacetone phosphate (DAP) and hydrogen peroxide. The hydrogen peroxide can then be reacted with any of a variety of dye precursors to produce a measurable color change. For example, a quinoneimine dye can be produced by reacting the hydrogen peroxide with 4-aminoantipyrine (with comprises sodium-N-ethyl-N-(3-sulfopropyl) m-anisidine (ESPA), p-chlorophenol, or 3,5-dichloro-2-hydoxybenzene sulfonate (DHBS)) in the presence of a peroxidase. These methods are preferred when the wood pulp sample includes less than about 100 ppm hydrogen peroxide or hydrosulfite before lipase treatment.

In another embodiment, glycerol, glycerol-1-phosphate or glycerol-3-phosphate is reacted with oxidized nicotinamide adenine dinucleotide ($NAD^+$) to form reduced nicotinamide adenine dinucleotide (NADH). The NADH can then be reacted with any of a variety of dye precursors to produce a measurable color change. For example, a formazan dye can be produced by reacting the NADH with 2-(p-iodophenyl)-3-p-nitrophenyl-5-phenyltetrazolium chloride (INT) or with nitro blue tetrazolium (NBT), in the presence of a diaphorase. These methods are particularly useful when the wood pulp sample comprises more than about 100 ppm hydrogen peroxide or hydrosulfite before lipase treatment.

In other embodiments, the glycerol is enzymatically reacted with adenosine triphosphate (ATP). In a preferred embodiment, the glycerol is reacted with adenosine triphosphate in the presence of a glycerol kinase to produce adenosine-5'-diphosphate (ADP). The ADP can then be reacted with phosphoenol pyruvate to produce pyruvate. Pyruvate can then be reacted with a dye precursor to produce a detectable change in light absorbance. For example, $NAD^+$ can be produced by reacting the pyruvate with NADH in the presence of a lactate dehydrogenase.

It is also possible to measure the amount of fatty acids, rather than glycerol, produced by the enzymatic hydrolysis of triglycerides. For example, fatty acids can be detected using any of a variety of known methods, including, but not limited to, high performance liquid chromatography, gas chromatography, thin layer chromatography, nuclear magnetic resonance imaging, mass spectroscopy, flame ionization detection, and gas-liquid chromatography and titration techniques.

The methods can further include adding an effective amount of a fiber surface modifier to the wood pulp sample to liberate at least a portion, and preferably substantially all, of the depositable triglycerides from cellulosic fibers of the wood pulp sample. Representative examples of fiber surface modifiers include enzymes (e.g., cellulases, hemi-cellulases, xylanases, ligninases, pectinases, proteases, manninases, glucomanninases, arabinonases, and/or amylases), surfactants, polymeric additives, and polyelectrolytes.

In some embodiments, the step of determining the difference between the amount of glycerol or fatty acids present in the wood pulp sample comprises (1) producing or consuming a measurable electrochemical species during one or more reactions involving the glycerol or fatty acids present in the wood pulp sample, and (2) determining the change in concentration of the electrochemical species obtained as a result of treating the wood pulp sample with the lipolytic enzyme. Preferably, the determination of the change in concentration of the electrochemical species includes the use of an electrode assembly, which is particularly useful in a continuous or semi-continuous diagnostic process.

For example, the electrode assembly can include known methods and means for measuring a change in an electrical current or potential. Examples of such electrode assemblies can include an oxygen-sensing electrode or an ion-selective electrode. In a preferred embodiment, the change in concentration of the electrochemical species is determined potentiometrically. Examples of useful electrochemical species include, but are not limited to, oxygen and hydrogen peroxide. For example, a change in electrical current can be caused by the platinum-catalyzed reduction of hydrogen peroxide.

Methods and systems are also provided for enhancing the control of pitch in a pulp and paper mill, by determining the depositable triglyceride content in a suspension of wood pulp. The methods include (1) obtaining one or more wood pulp samples from a sampling point in a pulp and paper mill, (2) assaying for depositable triglycerides in the wood pulp sample, and (3) activating one or more pitch control measures, as needed, based on the depositable triglycerides assay obtained. The systems include a means for assaying for depositable triglycerides in a wood pulp sample obtained from one or more sample points in a pulp and paper mill, and a device for applying one or more pitch control measures, which is in operable communication with the means for assaying such that the device can be activated, as needed, in response to the depositable triglycerides assay. Preferably, the pitch control measures are activated automatically in response to the depositable triglycerides assay. The means for assaying for the depositable triglycerides preferably utilizes one or more of the enzymatic methods described herein. The means for assaying desirably can include an electrode assembly suitable for measuring, preferably continuously, the change in concentration of an electrochemical species, which change is produced by treating the wood pulp sample with a lipolytic enzyme.

DETAILED DESCRIPTION OF THE INVENTION

Figure 1:
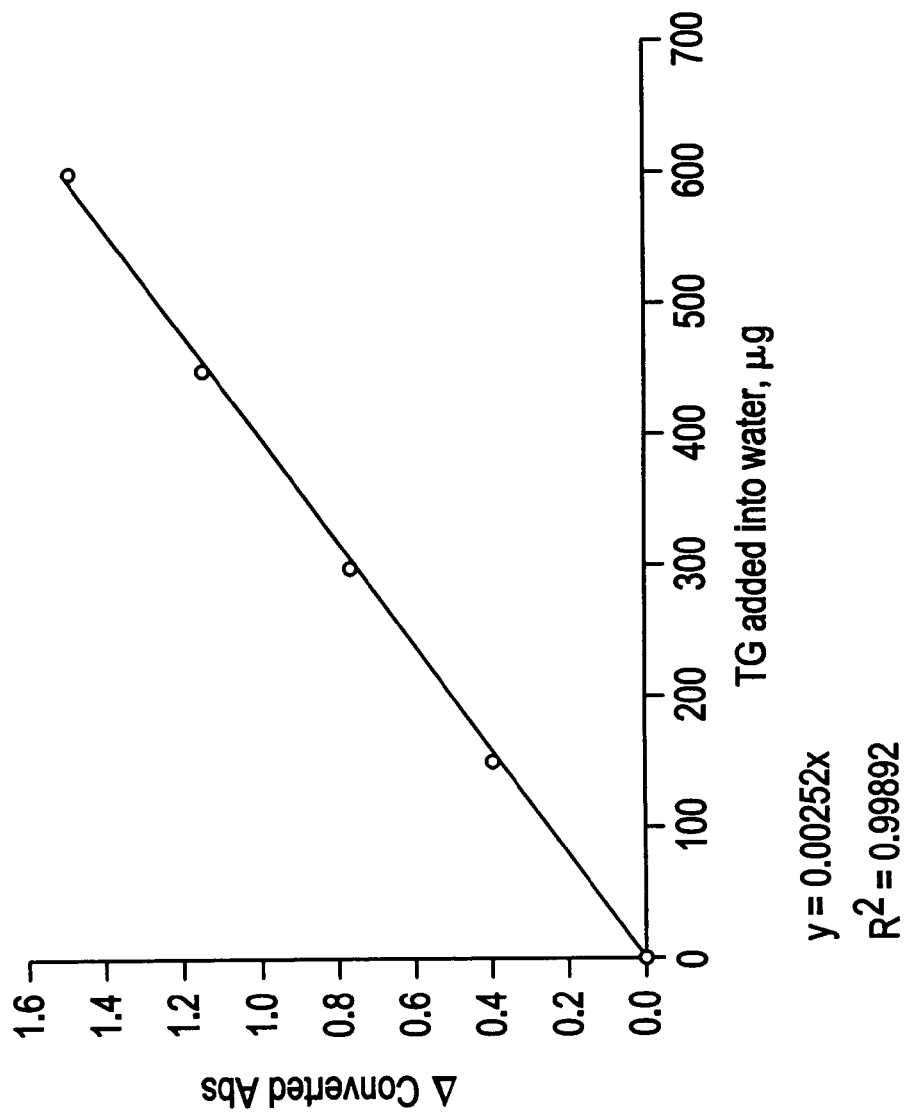
FIG. 1 is a graph of Δ converted absorbance of distilled water with triglycerides versus amount of triglycerides added to the distilled water.

Methods have been developed for use as a quick, portable, accurate, and low cost assay for assessing the amount of depositable triglycerides ("TG") present at various sample points in paper mills, which serve as a particularly important diagnostic tool for use in predicting and controlling the undesirable and deleterious deposition of pitch on paper machine components.

As used herein, the term "depositable triglycerides" refers to triglycerides residing on the surface of the pulp fibers as well as free triglycerides suspended in the process water with the pulp fibers or free triglycerides present in process water from which pulp fibers have been separated, such as whitewater. This is in contrast to the total triglycerides, which includes triglycerides trapped within the pulp fibers, which typically do not contribute to pitch deposition, but which are included in the total organic extractive content of the pulp. There can commonly be a poor correlation between the quantity of trapped or total triglycerides and the amount of pitch deposition observed.

I. The Methods for Analyzing Depositable Triglycerides

The preferred method for determining the depositable triglycerides content in a wood pulp sample comprises (1) reacting the depositable triglycerides in a wood pulp sample in the presence of a lipolytic enzyme to form glycerol and fatty acids, and then (2) determining the difference between the amount of glycerol or fatty acids present in the wood pulp sample before and after treatment with the lipolytic enzyme. In preferred embodiments, the second step involves (a) forming a measurable species from one or more reactions, in which the glycerol or fatty acids present in the wood pulp sample is a reactant, and then (b) obtaining a quantitative measurement of the measurable species present in the sample before and after lipase treatment. A wide variety of methods that have been developed to assay for triglycerides in biological applications also can be adapted for use in assaying for pulp triglycerides as described herein.

The preferred methods advantageously can be used as a diagnostic tool to analyze paper machine deposition problems online as they occur because of the substantially shorter assay time as compared to currently used, extraction-based methods. The TG assay can be conducted in preferably less than 6 hours, more preferably less than 4 hours, more preferably less than 2 hours, and most preferably less than 1 hour (e.g., less than 30 minutes, less than 20 minutes).

The method for determining the depositable triglycerides content can be conducted in a batch process (e.g., where samples are collected periodically and the test is conducted offline). Alternatively, the method for determining the depositable triglycerides content can be conducted in a continuous or semi-continuous process (e.g., online sampling/analysis).

A. Wood Pulp and Sample Points

The triglyceride analytical methods described herein can be applied to any essentially wood pulp sample. As used herein, the term "wood pulp sample" includes wood pulp suspensions, wood pulp fibers, and process water taken from essentially any sampling point in the wet end of a paper mill. The sampling point can be any point in the mill where pitch problems may exist. Representative examples of sample points include the low density chest (LD), which is a storage chest for pulp; the high density chest (HD), which is another storage chest for pulp; the decker, which thickens the pulp; the whitewater sample, which is a sample of the water inside the system loop; the blend chest; the headbox, which is the location just before the paper machine where the stock is prepared for the paper making process; and the paper machine (PM) where the paper is actually made.

These methods are particularly useful in paper mills that use a mechanical pulp. The methods are also useful with other pulps, such as Kraft and other chemical pulps.

B. Enzymatic Hydrolysis of the Triglycerides

The depositable triglycerides in a wood pulp sample are reduced (i.e. hydrolyzed) in the presence of a lipolytic enzyme to form glycerol and fatty acids.

Preferably, the lipolytic enzyme is a triacylglycerol lipase. Suitable lipases for the hydrolysis of triglycerides can be derived from plant, animal, or preferably microbial sources. Representative examples of sources for microbial lipases include *Candida rugosa, Rhizopus arrhizus*, and *Chromobacterium viscosum*.

Other suitable lipolytic enzymes belong to the family of carboxylic ester hydrolases. Representative examples of these include phospholipases, lipoprotein lipase, and acylglycerol lipase.

Alternatively, the lipolytic enzyme can be a non-lipase enzyme. For example, the lipolytic enzyme could be a carboxylesterase, such as acetyl esterase or aceyl esterase, which hydrolyze lower fatty acid esters. Examples of other suitable lipolytic enzymes include cholesterol esterase, which hydrolyses steroid esters, which can be used in combination with the lipase, e.g., as described in U.S. Pat. No. 4,259,440.

C. Detection of Change in Glycerol or Fatty Acid Concentration

The step of determining the difference between the amount of glycerol or fatty acids present in the wood pulp sample before and after treatment with the lipolytic enzyme can be performed using a variety of different techniques and reaction sequences. These techniques are desirably conducted rapidly, simply, accurately, and at low cost. In a preferred embodiment, the step is highly automated and suitable for use in continuous or semi-continuous diagnostic equipment. In another preferred embodiment, the step is conducted as a batch process, for example, in which pulp samples are collected periodically and tested offline (e.g., periodic manual sampling and then field or laboratory testing of these samples).

In preferred embodiments, the detection of change in glycerol or fatty acids involves (a) forming a measurable species from one or more reactions, in which the glycerol or fatty acids present in the wood pulp sample is a reactant, and then (b) obtaining a quantitative measurement of the measurable species present in the sample. For example, a comparison is made between the concentration of the glycerol in a wood pulp suspension before and after treatment with the lipolytic enzyme. The selection of a measurable chemical species to produce goes hand-in-hand with the selection of the desired measurement means.

In a preferred embodiment, the method is an enzyme-based colorimetric method that uses a spectrophotometer for detection. It generally takes only between about 20 and 30 minutes to assay a set of samples using such a method. The results are accurate and reproducible, and the method advantageously does not require use of the volatile organic compounds and solvents needed for use with extraction-based methods. The method also measures surface triglyceride content in the pulp and in the water, which correlates directly with the surface pitch content, which in turn directly relates to pitch deposition problems.

In other embodiments, non-colorimetric methods are used to determine the depositable triglyceride content in a wood pulp sample. Representative examples of non-colorimetric methods employ tests based on turbidities, titrations, impacts of electrical current arrays, or spectroscopic methods such as GC, HPLC, and NMR.

(a) Glycerol Detection

A variety of reaction sequences can be used to convert the glycerol to an easily quantifiable, measurable species. Glycerol detection is preferred for its low cost, portability, accuracy, and short assay time.

In preferred embodiments, the glycerol is enzymatically reacted in a reaction sequence that produces the measurable species. For example, the glycerol can be phosphorylated to produce glycerol-1-phosphate or glycerol-3-phosphate. In a preferred embodiment, glycerol, glycerol-1-phosphate, or glycerol-3-phosphate is then enzymatically oxidized with an electron acceptor.

Preferred examples of electron acceptors include oxygen ($O_2$), nicotinamide adenine dinucleotide ($NAD^+$), and nicotinamide adenine dinucleotide phosphate ($NADP^+$). Certain indolphenols, potassium ferricyanide, and certain tetrazolium salts can also be used as electron acceptors. In one embodiment, glycerol-1-phosphate or glycerol-3-phosphate can be reacted with oxygen ($O_2$) to form dihydroxyacetone phosphate (DAP) and hydrogen peroxide. The hydrogen peroxide can then be reacted with any one of a variety of dye precursors to produce a measurable color change, which can be quantified for example using a spectrophotometer. For example, a quinoneimine dye can be produced by reacting the hydrogen peroxide with 4-aminoantipyrine (which comprises sodium-N-ethyl-N-(3-sulfopropyl) m-anisidine (ESPA), p-chlorophenol, or 3,5-dichloro-2-hydoxybenzene sulfonate (DHBS)) in the presence of a peroxidase. These methods are preferred when the wood pulp sample includes less than about 100 ppm hydrogen peroxide or hydrosulfite before lipase treatment.

In another embodiment, glycerol, glycerol-1-phosphate or glycerol-3-phosphate is reacted with nicotinamide adenine dinucleotide ($NAD^+$) to form reduced (NADH). Like the hydrogen peroxide, the NADH can then be reacted with any one of a variety of dye precursors to produce a measurable color change. For example, a formazan dye can be produced by reacting the NADH with 2-(p-iodophenyl)-3-p-nitrophenyl-5-phenyltetrazolium chloride (INT) or with nitro blue tetrazolium (NBT), in the presence of a diaphorase. Any tetrazolium salt can be used in place of INT or NBT. Representative examples of other such tetrazolium salts include 3-(4',5'-dimethyl-thiazolyl-2)-2,4-diphenyltetetrazolium bromide (MTT); 2,2',5,5'-tetra-(p-nitrophenyl)-3,3'-(3-dimethoxy-4-diphenylene)-ditetrazolium chloride (TT); and neotetrazolium chloride (NT). These methods are particularly useful when the wood pulp sample comprises more than about 100 ppm hydrogen peroxide or hydrosulfite before lipase treatment.

In other embodiments, the glycerol is enzymatically reacted with adenosine triphosphate (ATP). In a preferred embodiment, the glycerol is reacted with adenosine triphosphate in the presence of a glycerol kinase to produce adenosine-5'-diphosphate (ADP). The ADP can then be reacted with phosphoenol pyruvate to produce pyruvate. Pyruvate can then be reacted with a dye precursor to produce a measurable color change. For example, NAD can be produced by reacting the pyruvate with NADH in the presence of a lactate dehydrogenase. NAD can be detected spectrophotometrically at 340 nm.

An iterative approach with known triglyceride concentrations can be used to correlate the absorbance of the sample to a quantitative triglyceride concentration. The correlation between absorbance and triglyceride concentration for a specific pulp sample is a function of each tree species and each pulp mill's water system, but can be readily determined by using an enzymatic calorimetric triglyceride analysis procedure to measure the absorbance of the same pulp samples with varied amounts of added triglyceride standard.

The absorbance analysis can be conducted using essentially any commercially available spectrophotometer operable at a useful wavelength. The spectrophotometer preferably is portable, such as the HACH DR/2000. In an alternative embodiment, the methods described herein can be adapted to measure transmittance (which is related to absorbance) and the surface triglyceride results calculated accordingly.

The particular method to be used may depend on the type of pulp to be analyzed, as well as on other constituents present in the sample. For example, at least one method is preferred for pulp samples that are free of, or contain less than, 100 ppm hydrogen peroxide or hydrosulfite, while at least one different method is preferred for pulp samples containing more than 100 ppm hydrogen peroxide or hydrosulfite. This is because it was discovered that residual hydrogen peroxide and hydrosulfite (e.g., used as bleaching agents) can interfere with the results obtained with a method in which hydrogen peroxide and peroxidase are intermediate products and test materials in that method.

The following are some non-limiting, specific examples of the various reaction sequences that can be employed.

Assay (1)

In this preferred embodiment, which is preferred for pulp without (or less than 100 ppm) residual hydrogen peroxide or hydrosulfite, the assay utilizes the following enzyme-coupled reactions:

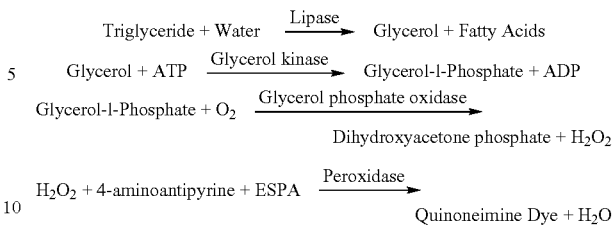

The triglycerides are reduced by a lipase to glycerol and free fatty acids. The glycerol is reacted with adenosine triphosphate (ATP) to form adenosine-5'-diphosphate (ADP) and glycerol-1-phosphate, which reacts with oxygen to form dihydroxyacetone phosphate and peroxide. The peroxide reacts with 4-aminoantipyrine and sodium-N-ethyl-N-(3-sulfopropyl) m-anisidine (ESPA) to form quinoneimine dye and water.

From this series of reactions, the concentration of quinoneimine dye formed as the final product is directly proportional to the concentration of depositable triglycerides initially present in the sample and can be detected with a spectrophotometer. In a preferred embodiment, absorbance is measured at a wavelength of 540 nm, which is the optimum wavelength where absorbance is at its maximum value, but a range of other wavelengths, e.g., between about 500 and 580 nm, can also be used.

In a preferred embodiment of a method employing this reaction sequence, three reagents are prepared and used in the assay: (1) a first triglyceride reagent ("PC-A"), which reacts with glycerol to form a dye; (2) a second triglyceride reagent ("PC-B"), which is a standard lipoprotein lipase; and (3) triolein standard, 99%. The reagents preferably are provided as a kit of parts including at least PC-A and PC-B, and optionally further including the triolein emulsion standard. These kits may further include assay equipment, such as test tube vials, filters, syringes, water bath, pipettes, timers, and/or a spectrophotometer.

The PC-A preferably includes ATP, magnesium salt (or other divalent metal ion source), 4-aminoantipyrine, ESPA, glycerol kinase, glycerol phosphate oxidase, and peroxidase, and optionally includes stabilizers, fillers, and preservatives. Glycerol kinase requires $Mg^{+2}$ or another divalent metal ion, such as $Mn^{+2}$, for activity. Table 1 lists suitable, preferred, and more preferred ranges for the components of PC-A.

TABLE 1

| | PC-A Components and Preferred Concentrations of Each | | |
|---|---|---|---|
| Component | Most Preferred Concentration | Preferred Concentration | Suitable Concentration |
| ATP | 0.375 mM | 0.3 to 0.45 mM | 0.05 to 50 mM |
| Magnesium salt | 3.75 mM | 3.0 to 4.5 mM | 0.1 to 500 mM |
| 4-aminoantipyrine | 0.188 mM | 0.1 to 0.25 mM | 0.01 to 50 mM |
| (ESPA) | 2.11 mM | 0.5 to 10 mM | 0.01 to 300 mM |
| Glycerol kinase | 1,250 U/L | a1,000 to 1,500 U/L | 10 to 50,000 U/L |
| Glycerol phosphate oxidase | 2,500 U/L | 2,000 to 3,000 U/L | 100 to 50,000 U/L |
| Peroxidase | 2,500 U/L | 2,000 to 3,000 U/L | 100 to 50,000 U/L |

In other embodiments, peroxidase, ESPA, and 4-aminoantipyrine can be substituted with functionally equivalent materials. The peroxidase catalyzes the oxidation of a chromogen of peroxidase in the presence of hydrogen peroxide. Examples of other substances that are not peroxidases, but possess peroxidase-like activity include iron sulfocyanate, iron tannate, ferrous ferrocyanide, and chromic salts absorbed in silica gel. ESPA and 4-aminoantipyrine combine with hydrogen peroxide in the presence of peroxidase to produce quinoneimine dye.

Chromogens of peroxidase are color-forming substrates, which produce a color change in the presence of hydrogen peroxide and peroxidase. Representative examples of peroxidase chromogens include monoamines, such as aniline and its derivatives; diamines, such as ortho-phenylenediamine, dianisidine, and benzidine; phenols such as thymol; polyphenols such as catechol; aromatic acids such salicyclic acid; leuco dyes such as leucomalachite green; and colored dyes such as 2,6-dichlorophenolindophenol.

In a preferred embodiment, PC-B is composed of 250,000 U/L lipase (microbial), nonreactive stabilizers and fillers, and sodium azide 0.05% added as a preservative. In addition, a 3000 mg/L triolein emulsion standard is preferred.

The PC-A and PC-B reagent compositions preferably are stabilized with a non-reactive stabilizer, such as sorbitol, and preserved with a preservative, such as sodium azide at a concentration of 0.05%. Examples of suitable buffers for use in the reagent composition include Tris(hydroxymethyl) amino ethane (TRIS) and/or 3-(4-morpholino)propane-sulfonic acid (MOPS). In preferred embodiments, the pH of PC-A and PC-B are between pH 6.5 and 8.5. More preferably, the pH of PC-A and PC-B are 7.0 and 7.8, respectively.

erol-1-phosphate which reacts with nicotinamide adenine dinucleotide (NAD) to form dihyroxyacetone phosphate (DAP) and NADH (the reduced form of NAD). The reduction of NAD is catalyzed by glycerol-1-phosphate dehydrogenase (G-1-PDH). NADH reacts with 2-(p-iodophenyl)-3-p-nitrophenyl-5-phenyltetrazolium chloride (INT) to form formazan dye and NAD. This reaction is catalyzed by diaphorase.

From this series of reactions, the concentration of quinoneimine dye formed as the final product is directly proportional to the concentration of depositable triglycerides initially present in the sample and can be detected with a spectrophotometer, as described above.

In a preferred embodiment of a method employing this reaction sequence, three reagents are prepared and used in the assay: (1) a first triglyceride reagent ("PC-Y") comprising INT, which reacts with glycerol to form a dye; (2) a second triglyceride reagent ("PC-Z"), which is a standard lipoprotein lipase; and (3) triolein standard, 99%. The reagents preferably are provided as a kit of parts including at least PC-Y and PC-Z, and optionally further including the triolein emulsion standard. These kits may further include assay equipment, such as test tube vials, filters, syringes, water bath, pipettes, timers, and/or a spectrophotometer.

The PC-Y preferably includes ATP, magnesium salt (or other divalent metal ion source), NAD, INT, glycerol kinase, G-1-PDH, and diaphorase, and optionally includes stabilizers, fillers, and preservatives. Glycerol kinase requires $Mg^{+2}$ or another divalent metal ion, such as $Mn^{+2}$, for activity. Table 2 lists suitable, preferred, and more preferred ranges for the reagents of PC-Y.

TABLE 2

PC-Y Components and Preferred Concentrations of Each

| Component | Most Preferred Concentration | Preferred Concentration | Suitable Concentration |
|---|---|---|---|
| ATP | 2.0 mM | 1.5 to 2.5 mM | 0.05 to 50 mM |
| NAD | 2.0 mM | 1.5 to 2.5 mM | 0.05 to 50 mM |
| Magnesium ions | 3.0 mM | 2.0 to 4.0 mM | 0.1 to 500 mM |
| INT | 1.0 mM | 0.5 to 10 mM | 0.01 to 100 mM |
| Glycerol kinase | 200 U/L | 150 to 250 U/L | 10 to 50,000 U/L |
| G-1-PDH | 4,000 U/L | 3,000 to 5,000 U/L | 100 to 50,000 U/L |
| Diaphorase | 455 U/L | 300 to 600 U/L | 10 to 50,000 U/L |

Assay (2)

In this preferred embodiment, which is preferred for pulp with residual (e.g., greater than 100 ppm) hydrogen peroxide or hydrosulfite, the assay utilizes the following enzyme-coupled reactions:

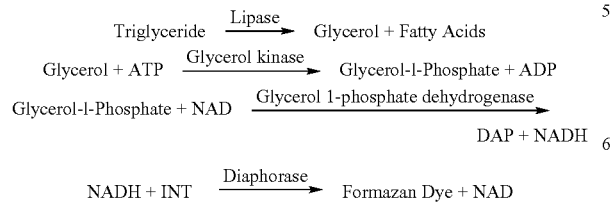

The triglycerides are reduced to glycerol and fatty acids by a lipase. The glycerol is reacted with adenosine triphosphate (ATP) to form adenosine-5'-diphosphate (ADP) and glyc- In a preferred embodiment, PC-Z is composed of 250,000 U/L lipase (microbial), nonreactive stabilizers and fillers, and sodium azide 0.05% added as a preservative. In addition, a 3000 mg/L triolein emulsion standard is preferred. Suitable lipases, stabilizers, preservatives, and buffers for the PC-Y and PC-Z reagents are the same as those described above for the PC-A and PC-B reagents.

In alternative embodiments of the method, PC-Y reagent components can be substituted with functionally equivalent materials. For example, 2-(p-iodophenyl)-3-(p)-nitrophenyl)-5-phenyl tetrazolium chloride (INT) is classified as a tetrazolium salt. Any tetrazolium salt can be used in place of INT. Representative examples of other such tetrazolium salts include nitro blue tetrazolium chloride (NBT); 3-(4', 5'-dimethyl-thiazolyl-2)-2,4-diphenyltetetrazolium bromide (MTT); 2,2',5,5'-tetra-(p-nitrophenyl)-3,3'-(3-dimethoxy-4-diphenylene)-ditetrazolium chloride (TT); and neotetrazolium chloride (NT).

Diaphorase is an electron transfer agent. Representative examples of other electron transfer agents that can be used with tetrazolium salts include phenazine methosulfate (PMS); 8-dimethylamino-2,3-benzophenoxazine (Meldola blue); and 1-methoxy-5-methlyphenazinium-methylsulfate.

NAD is classified as a pyrine dinucleotide. Representative examples of other pyrine dinucleotides that can be used in place of NAD include NADP (nicotinamide adenine dinucleotide phosphate) and derivatives of NAD.

Assay (3)

This embodiment utilizes the following enzyme-coupled reactions:

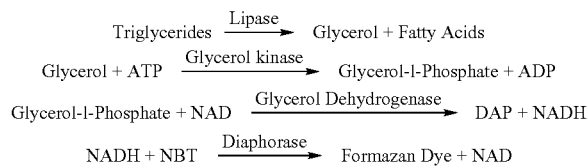

Assay (4)

This embodiment utilizes the following enzyme-coupled reactions:

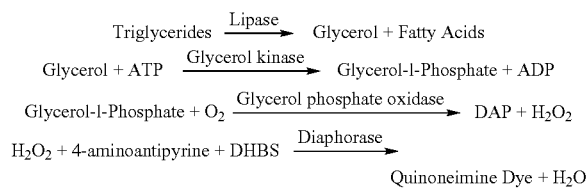

Assay (5)

This embodiment utilizes the following enzyme-coupled reactions:

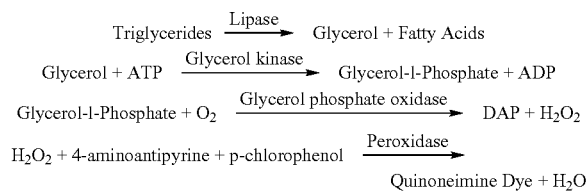

Assay (6)

This embodiment utilizes the following enzyme-coupled reactions:

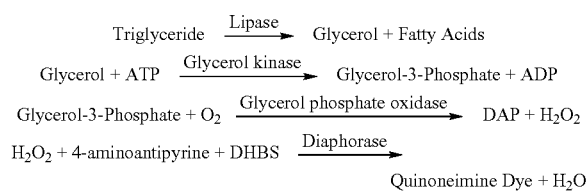

Assay (7)

This embodiment utilizes the following enzyme-coupled reactions:

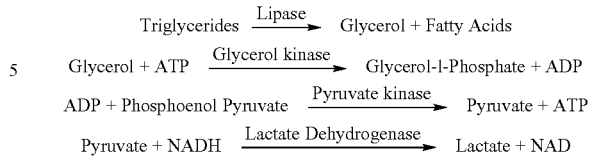

Assay (8)

This embodiment utilizes the following enzyme-coupled reactions:

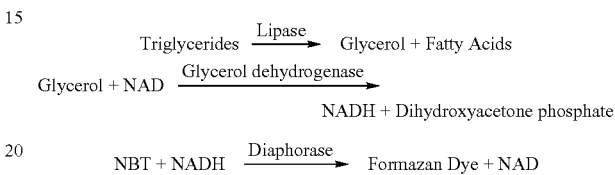

Like Assays 1 and 2, Assays 3 to 8 can be readily modified using equivalent components, and can be conducted by preparing and using reagents analogous to PC-A, PC-B, PC-Y, and/or PC-Z.

The reagents for these assays are not limited to liquid forms. For example, it is envisioned that the enzymes and/or other reagents can be incorporated onto test strips, as known in the art. See, e.g., U.S. Pat. Nos. 5,110,724 and 5,597,532. Such test strips could provide a ready, easy-to-use format for assaying for TG. A microprocessor-controlled reflectance photometer could be used to perform a reflectance measurement on dry test strips containing the reagents needed to perform the assay, and then calculate a quantitative triglyceride value as described in U.S. Pat. No. 5,597,532.

Representative examples of other method steps that can be used to assay glycerol are described in U.S. Pat. Nos. 4,273,870; 4,394,445; 4,142,938; 4,245,041; 4,241,178; 4,223,090; 5,221,615; 4,923,796; 4,259,440; 4,309,502; and 4,636,465.

(b) Fatty Acid Detection

A variety of reaction sequences can be used to convert the free fatty acids to a quantifiable, measurable species. For example, the quantitative measurement can be obtained from a test measuring a property selected from concentration of an electrochemical species, spectrometric characteristics, and chromatographic characteristics. Representative examples of known methods for fatty acid detection include HPLC, gas chromatography, TLC, nuclear magnetic resonance, mass spectroscopy, flame ionization detection, gas-liquid chromatography, and titration methods. In one embodiment, pH is measured to assess the change in fatty acids present (see, e.g., U.S. Pat. No. 4,713,165).

D. Optional Processing Agents

Optionally, fiber surface modifiers can be added to the sample with the lipase to modify the surface of the wood pulp fibers to help liberate surface triglycerides. Representative examples of such fiber surface modifiers include other enzymes, surfactants, and polymeric additives. Examples of such enzymes include, but are not limited to, cellulases, hemi-cellulases, xylanases, ligninases, pectinases, proteases, manninases, glucomanninases, arabinonases, and amylases. Representative surfactants include cationic, anionic, non-ionic, and amphoteric surfactants. Polymeric additives include for example polyelectrolytes.

E. Detection By Electrochemical Means

In a preferred embodiment, the step of determining the difference between the amount of glycerol or fatty acids present in the wood pulp sample includes (i) producing or consuming a measurable electrochemical species during one or more reactions involving the glycerol or fatty acids present in the wood pulp sample, and (ii) determining the change in concentration of the electrochemical species obtained as a result of treating the wood pulp sample with the lipolytic enzyme.

The determination of the change in concentration of the electrochemical species typically and preferably utilizes an electrode assembly. For example, the electrode assembly can include an oxygen-sensing electrode or an ion-selective electrode, as known in the art. Typically, the electrodes operate by electrochemically active species undergoing electrochemical reactions (oxidation or reduction) at the surface of the electrode. The rate of these reactions is related to the reactivity of the species, the electrode material, and the electrical potential applied to the electrode. The electrochemical species can be, for example, oxygen or hydrogen peroxide. The electrode assembly can measure a change in an electrical current, for example, a change caused by metal (e.g., platinum) catalyzed reduction of hydrogen peroxide. In one embodiment of the electrode assembly, the change in concentration of the electrochemical species can be determined potentiometrically.

In one embodiment, glycerol is reacted with ATP to form glycerol-1-phosphate and ADP, wherein the reaction is catalyzed by glycerol kinase. The glycerol-1-phosphate reacts with oxygen in a reaction catalyzed by glycerol phosphate oxidase to form dihydroxyacetone phosphate and hydrogen peroxide. The hydrogen peroxide is then converted to a measurable electrical current upon the electrochemical reduction by platinum. The electrical current can be measured using an electrode assembly and sensors known in the art. For, example, U.S. Pat. No. 5,989,409 to Kurnik, et al. (which is incorporated herein) describes a method and apparatus for glucose sensing, which can be modified from glucose sensing to glycerol sensing by changing the biochemical reaction sequence to that described above.

In another embodiment, an oxygen-sensor is used to measure oxygen consumption or production from an enzymatic reaction sequence which corresponds to glycerol or fatty acids produced by TG hydrolysis. See, for example, U.S. Pat. No. 4,045,297, which describes an oxygen-sensing electrode assembly using an enzyme coupled reaction series. For example, the reaction series could be as follows:

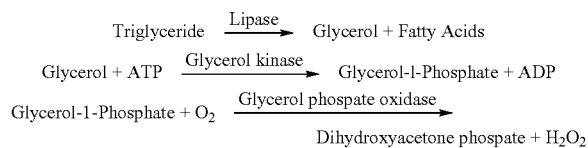

The uptake of oxygen is proportional to the amount of surface triglycerides present in the pulp sample. One can use known concentrations of triglycerides to determine a relationship between oxygen uptake and triglyceride concentration.

In another embodiment, electric field potentiation is used to measure the results of an enzymatic reaction sequence corresponding to glycerol or fatty acids produced by TG hydrolysis. Preferably, such methods are carried out using ion-selective electrodes. The change in ion concentration (e.g., pH) corresponds to the change in electrical potential. The electrode assembly can include an immobilized enzyme used in the reaction sequence. See, e.g., U.S. Pat. No. 4,713,165. For example, the triglyceride present in the wood pulp could be reacted with lipase to produce cationic fatty acids whose production is measured by a change in pH of the sample. The triglyceride concentration could be quantified by measuring the pH change in samples of known triglyceride concentration to determine a relationship between triglyceride concentration and pH change.

II. TG Assay Devices

Figure 12:
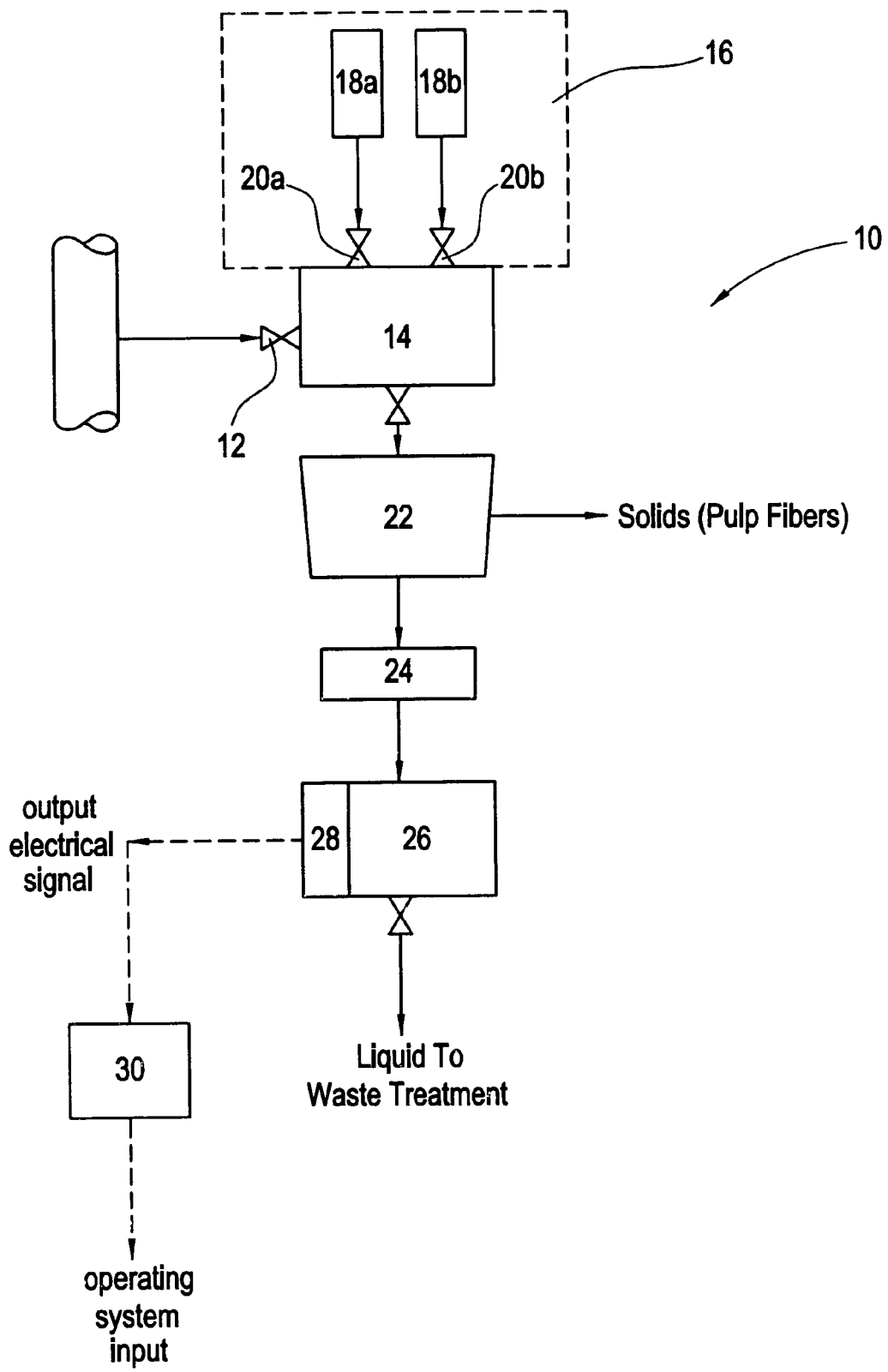
FIG. 12 is a schematic of a device for conducting an on-line triglyceride assay.

One example of device for performing the triglyceride assay on-line is illustrated schematically in FIG. 12. As used herein, the term "on-line" in reference to assays, tests, or measurements refers to processes of, or steps involved in, assays, tests, or measurements which do not require human intervention, i.e. the steps or tests can be carried out and a result obtained without manually taking the sample, manually mixing the sample with a reagent, or manually measuring a resulting property.

The TG assay device 10 includes a sampling means, shown as valve 12, for withdrawing an aliquot of pulp from a process 11. The sampling means diverts a select quantity of wood pulp sample into a reaction vessel 14. This can be done using either a positive pressure flow or by physical diversion to direct the aliquot from the process. For example, a valve can be opened long enough to allow the process pulp flowing under pressure through a pipe to be diverted into a reaction vessel at ambient (atmospheric) pressure, and then the valve can be closed. A deflector (not shown) can be used to facilitate pushing the pulp into the vessel. The reaction vessel, which could be a closed stainless steel container, preferably includes an agitation means (not shown) for mixing the pulp sample and reagents together. Examples of agitation means include static and dynamic mixers, circulation pumps, and the like, or the reaction chamber could be made to mechanically shake or vibrate to facilitate mixing.

The device 10 also includes a reagent supply means 16, which includes reagent storage vessels 18a and 18b and corresponding reagent control means 20a and 20b, for controlling the introduction of reagent formulation A (which contains all the reagents needed to measure glycerol or fatty acid concentration before/without the lipolytic enzyme reaction) and reagent formulation B (which contains all the reagents needed to measure glycerol or fatty acid concentration after/with lipolytic enzyme reaction). Reagent control means 20a and 20b control the time and amount of addition of reagent formulations A and B into reaction vessel 14, thereby permitting the reagents to contact and react with the wood pulp sample contained therein. These reagents may be introduced in either liquid or solid form. For example, a solid form of the reagents can use a paper sheet or strip as a carrier or delivery vehicle.

The device 10 further has a separator means for separating the pulp fibers from the filtrate following completion of the reaction sequence. This separator means can include a filtration unit, as known in the art. In the embodiment shown in FIG. 12, the separator means includes a centrifuge 22 and an optional secondary filter 24. The centrifuge 22 can serve as both the reaction vessel 14 and the separator means, although they are shown in FIG. 12 as discrete elements. In typical operation of the centrifuge, the reacted pulp suspension is spun in a perforated rotating basket, which causes the aqueous solution (i.e. the pulp dispersion medium) to filter through small perforations in the rotating basket, while retaining the dried pulp fibers on the inside surface of the rotating basket (or on a filter cloth secured therein). The aqueous solution, i.e. the filtrate, then flows to and through the optional secondary filter 24 and into sensing chamber 26.

In sensing chamber 26, the concentration of the measurable species is measured with measuring device 28, which, for example, can include a spectrophotometer or electrode assembly. The measuring device 28 typically produces an electrical signal corresponding to the measured value (e.g., pH, transmittance, change in voltage or current, etc.), which can be routed through a microprocessor (not shown) and therein converted using pre-programmed metrics into a numerical value for display and use by an operator of the pulp and papermaking process. In one variation, the electrical signal can be coupled with an on-line pulp consistency meter (not shown) to give a quantitative TG value, e.g., percentage of TG in the dry pulp slurry at point X in the process.

The device also can optionally include means for recording or tracking the measured triglycerides over time. For example, output data from the device 10 could be depicted as a line graph on a computer monitor 30 in a pulp/paper mill control room. This data also can be used to manually or automatically to regulate one or more pitch control measures (detailed below). In other words, TG data from the device can be used as an input value for a mill operator or computer controller to manage the triglycerides in the mill process in order to prevent or minimize pitch deposits. Accordingly, in one embodiment, the device is operably linked with a computer process controller for the mill, and in particular, is operably linked to a pitch control system.

Following completion of this assay scheme, the equipment can be automatically purged and cleaned with water or a washing solution for later re-use, e.g., at a preset interval. The centrifuge and polishing filter typically would be back-flushed or otherwise washed after each batch (i.e. aliquot) is processed.

III. Using the TG Analytic Methods

It is contemplated that the triglyceride assay methods described herein can be automated and integrated into a control (feedback) loop to facilitate automation of a pitch control system. For example, a continuous brightness meter or electromagnetic field could be accurately standardized for use (using the assay methods described herein). Such continuous meters could be used as a proxy to determine relative levels of the material desired to be tracked, and need not identify specific nominal levels.

As used herein, a "pitch control system", "pitch control measure," or "system for pitch control" refers to any methods, equipment, chemicals, enzymes, or combinations thereof applied to one or more processes in a pulp mill and/or paper mill to reduce the depositable pitch content in the process materials (e.g., wood pulp and process water) in order to control the deposition of pitch onto the mill equipment, the paper product, or both. Examples of pitch control measures include control of mill operating parameters (e.g., temperatures, pH, tank levels, flow rates, wood yard management, degree of fresh water usage, and the like) and control of dosing of a pitch control additive (e.g., enzymes, alum, polymers, talc, and the like), for the purpose of controlling the triglycerides in the mill in order to prevent or minimize pitch deposits. Representative examples of pitch control systems include systems for cationic fixation of pitch with alum or cationic polymers, for pitch dispersion with surfactants at alkaline conditions, for pitch absorption with talc, for pitch chelation with heavy metals, and for enzymatic pitch control. Pitch control systems are described, for example, in U.S. Pat. No. 5,256,252 to Sarkar, et al., U.S. Pat. No. 5,176,796 to Irie et al., and U.S. Pat. No. 5,667,634 to Fujita et al., which are incorporated herein by reference.

Methods and systems are also provided for enhancing the control of pitch in a pulp and paper mill, by determining the depositable triglyceride content in a suspension of wood pulp. The methods include (1) obtaining one or more wood pulp samples from a sampling point in a pulp and paper mill, (2) assaying for depositable triglycerides in the wood pulp sample, and (3) activating one or more pitch control measures, as needed, based on the depositable triglycerides assay obtained. The systems include a means for assaying for depositable triglycerides in a wood pulp sample obtained from one or more sample points in a pulp and paper mill, and a device for applying one or more pitch control measures, which is in operable communication with the means for assaying such that the device can be activated, as needed, in response to the depositable triglycerides assay. Preferably, the pitch control measures are activated automatically in response to the depositable triglycerides assay. The means for assaying for the depositable triglycerides preferably utilizes one or more of the enzymatic methods described herein. The means for assaying desirably can include an electrode assembly suitable for measuring, preferably continuously, the change in concentration of an electrochemical species, which change is produced by treating the wood pulp sample with a lipolytic enzyme.

The present invention can be further understood with reference to the following non-limiting examples.

EXAMPLE 1

Enzymatic Colorimetric TG Method Using PC-A/PC-B

The triglycerides would be reduced to glycerol and fatty acids by a lipase. The glycerol would react with adenosine triphosphate (ATP) to form adenosine-5'-diphosphate (ADP) and glycerol-1-phosphate, which would react with oxygen to form dihydroxyacetone phosphate and peroxide. The peroxide would react with 4-aminoantipyrine and sodium-N-ethyl-N-(3-sulfopropyl) m-anisidine (ESPA) to form quinoneimine dye and water. From this series of reactions, the concentration of quinoneimine dye formed as the final product would be directly proportional to the concentration of depositable triglycerides initially present in the sample, which would be detected with a spectrophotometer at a wavelength of 540 nm.

Reagents

Three primary reagents (PC-A, PC-B, and triolein standard) would be used. The PC-A would have the following composition:

| | |
|---|---|
| ATP | 0.375 mM |
| Magnesium salt | 3.75 mM |
| 4-Aminoantipyrine | 0.188 mM |
| Sodium-N-ethyl-N-(3-sulfopropyl) m-aniside (ESPA) | 2.11 mM |
| Glycerol kinase (microbial) | 1250 U/L |
| Glycerol phosphate oxidase (microbial) | 2500 U/L |
| Peroxidase (horseradish) | 2500 U/L |
| Buffer | pH 7.0 ± 0.1 |
| Nonreactive stabilizers and fillers | |

The PC-B would have the following composition:

| | |
|---|---|
| Lipase (microbial) | 250,000 U/L |
| Nonreactive stabilizers and fillers | |

Sodium azide 0.05% would be added to both PC-A and PC-B as a preservative.

A 3000 mg/L triolein emulsion standard would be prepared by mixing 300 mg triolein with 9.6 g Triton X-100; heating the mixture until a clear single phase appears; adding 90 mL distilled water to the phase; mixing it uniformly; and then warming the solution and mixing it several times by inversion.

Procedure

The procedure would include determining the absorbance with lipase treatment, determining the absorbance without lipase treatment, and then calculating the triglyceride content based on the differences between the two absorbances.

(I) Determination of Absorbance with Lipase Treatment
A. Weigh 2.0 g of a sample of pulp of known consistency (preferably <1%) into a screw-capped tube. If the pulp consistency is much higher than 1%, dilute it to about 1% using distilled water.
B. Add 1.0 mL of distilled water.
C. Add 2.0 mL PC-A solution to the sample.
D. Add 0.5 mL PC-B solution to the sample and mix by inversion.
E. Incubate for 12 min. at 37° C., for example, with a heating block or water bath. Invert the tube every 3 min. to ensure the uniformity of the pulp solution.
F. Immediately place the tubes in ice cold water to stop the reaction.
G. Filter the pulp with a 0.45 μm glass fiber syringe filter, and place the filtrate into the tube.
H. Set the spectrophotometer wavelength at 540 nm and the absorbance reading to zero using distilled water as reference.
I. Read and record the absorbance at 540 nm of the filtrate sample ($A_{A+B}$).

(II) Determination of Absorbance without Lipase Treatment
A. Weigh 2.0 g of a sample of pulp of known consistency into the screw-capped tube.
B. Add 1.0 mL of distilled water.
C. Add 2.0 mL PC-A solution and mix.
D. Incubate for 12 min. at 37° C., for example with a heating block or water bath. Invert the tube every 3 min. to ensure the uniformity of the pulp solution.
E. Immediately place the tube in cold water to stop the reaction.
F. Filter the pulp with a 0.45 μm glass fiber syringe filter, and place the filtrate into the tube.
G. Set the spectrophotometer wavelength at 540 nm and the absorbance reading to zero using distilled water as reference.
H. Read and record the absorbance at 540 nm of the filtrate sample ($A_A$).

(II) Relating Absorbance to Triglyceride Concentration

A relative amount of depositable triglyceride would be determined from the difference between measured absorbance values $A_A$ and $A_{A+B}$. An iterative approach with known triglyceride concentrations can be used to correlate the absorbance of the sample to a quantitative triglyceride concentration.

EXAMPLE 2

Enzymatic Colorimetric TG Method Using PC-Y/PC-Z

The triglycerides would be reduced to glycerol and fatty acids by a lipase. The glycerol would be reacted with adenosine triphosphate (ATP) to form adenosine-5'-diphosphate (ADP) and glycerol-1-phosphate which would react with nicotinamide adenine dinucleotide (NAD) to form dihyroxyacetone phosphate (DAP) and NADH (the reduced form of NAD). The reduction of NAD would be catalyzed by glycerol-1-phosphate dehydrogenase (G-1-PDH). NADH reacts with 2-(p-iodophenyl)-3-p-nitrophenyl-5-phenyltetrazolium chloride (INT) to form formazan dye and NAD. This reaction would be catalyzed by diaphorase. From this series of reactions, the concentration of formazan dye formed as the final product would be directly proportional to the concentration of depositable triglycerides initially present in the sample and would be detected with a spectrophotometer at a wavelength of 500 nm.

Reagents

Three primary reagents (PC-Y, PC-Z, and triolein standard) would be used.

The PC-Y would have the following composition:

| | |
|---|---|
| ATP | 2.0 mM |
| NAD | 2.0 mM |
| Magnesium ions | 3.0 mM |
| INT | 1.0 mM |
| Glycerol kinase (microbial) | 200 U/L |
| G-1-PDH (rabbit muscle) | 4000 U/L |
| Diaphorase (microbial) | 455 U/L |
| Triton X-100 | 0.2% |
| Buffer | pH 7.8 ± 0.1 |
| Nonreactive stabilizers and fillers | |

The PC-Z would have the following composition:

| | |
|---|---|
| Lipase (microbial) | 250,000 U/L |
| Nonreactive stabilizers and fillers | |

Sodium azide 0.05% would be added to both PC-Y and PC-Z as a preservative.

For use, PC-Y and PC-Z solutions would be prepared by reconstituting dry PC-Y and PC-Z with a volume of deionized water into labeled vials. After addition of water, the vials would be stoppered and immediately mixed. A 3000 mg/L triolein emulsion standard would be prepared as described in Example 1.

Procedure

The procedure would include determining the absorbance with lipase treatment, determining the absorbance without lipase treatment, and then calculating the triglyceride content based on the differences between the two absorbances.

(I) Determination of Absorbance with Lipase Treatment
A. Weigh 2.0 g of a sample of pulp of known consistency into a screw-capped tube.
B. If there is hydrosulfite in the pulp sample at a concentration less than 1000 ppm, then add 1000 ppm of hydrogen peroxide to the pulp sample and let it incubate at room temperature for 5 minutes. In the unlikely event that the concentration exceeded 1000 ppm hydrosulfite, then additional hydrogen peroxide may need to be added.
C. Add 1.0 mL of distilled water.
D. Add 2.0 mL PC-Y solution to the sample.
E. Add 0.5 mL PC-Z solution to the sample and mix.
F. Incubate for 12 minute at 37° C. Invert the tube every 3 minutes to ensure the uniformity of the pulp solution.
G. Immediately place the tube in cold water to stop the reaction. As formazan dye tends to stick to the pulp, a surfactant, such as Triton X-100, t-octylphenoxypolyethoxyethanol, is added to the solution to release the dye from the pulp. The addition of about 0.2% Triton X-100 is usually a sufficient amount for dye release.
H. Filter the pulp with a 0.45 μm glass fiber syringe filter, and place the filtrate into the tube.
I. Set the spectrophotometer wavelength at 500 nm and the absorbance reading to zero using distilled water as reference.
J. Read and record the absorbance at 500 nm of the filtrate sample ($A_{Y+Z}$).

(II) Determination of Absorbance without Lipase Treatment
A. Weigh 2.0 g of a sample of pulp of known consistency into a screw-capped tube.
B. If there is hydrosulfite in the pulp sample at a concentration less than 1000 ppm, then add 1000 ppm of hydrogen peroxide to the pulp sample and allow it to incubate at room temperature for 5 minutes.
C. Add 1.0 mL of distilled water to the sample. For standardizing new pulps, add a total 1.0 mL of certain volume of Triolein emulsion and distilled water.
D. Add 2.0 mL PC-Y solution to the sample and mix.
E. Incubate for 12 min. at 37° C. Invert the tube every 3 min. to ensure the uniformity of the pulp solution.
F. Immediately place the tube in cold water to stop the reaction. Add surfactant, such as Triton X-100, t-octylphenoxypolyethoxyethanol, to the solution as needed to release the dye from the pulp. The addition of about 0.2% Triton X-100 is usually a sufficient amount for dye release.

bance values $A_Y$ and $A_{A+Z}$. An iterative approach with known triglyceride concentrations can be used to correlate the absorbance of the sample to a quantitative triglyceride concentration.

EXAMPLE 3

Testing the Enzymatic Colorimetric TG Method for Pulp

Test vials were prepared, containing 2 mL of water, to which 2 mL of PC-A was added along with varying amounts of triglycerides (standard concentration of 3000 mg/L) as shown in Table 3. The procedures of Example 1 were used to obtain the results.

For the sake of clarity, the actual measurement value that is taken when the sample is placed in the spectrophotometer is termed the "absorbance". "Converted absorbance" is the absorbance of the sample with lipase treatment multiplied by 1.1, the ratio of the total volume of the pulp suspension with and without the addition of lipase, minus the absorbance of the sample without lipase treatment. The "Δ converted absorbance" represents the normalized data values obtained by subtracting the converted absorbance value obtained for the sample with 0 micrograms of added triglycerides from all of the data points.

Results

The results shown in Table 3 are illustrated in FIG. 1. It can be seen from FIG. 1 that the absorbance versus triglyceride weight added into the water exhibits a linear relationship when triglycerides are less than 600 μg vial, suggesting that 600 μg is the maximum triglyceride weight that can be readily measured using the specifications of this technique. A slope of 0.00252 Abs/μg is obtained in FIG. 1.

TABLE 3

Results of Adding Triglycerides into Distilled Water

| Test No. | Water Sample volume mL | TG sample mL | TG sample μg | Distilled water mL | $A_A$ abs | $A_{A+B}$ abs | Converted abs | Δ Converted abs |
|---|---|---|---|---|---|---|---|---|
| 1 | 2 | 0 | 0 | 1.000 | 0.025 | 0.030 | 0.0080 | 0.0000 |
| 2 | 2 | 0.05 | 150 | 0.950 | 0.027 | 0.386 | 0.3976 | 0.3896 |
| 3 | 2 | 0.1 | 300 | 0.900 | 0.031 | 0.730 | 0.7720 | 0.7640 |
| 4 | 2 | 0.15 | 450 | 0.850 | 0.034 | 1.090 | 1.1650 | 1.1570 |
| 6 | 2 | 0.2 | 600 | 0.800 | 0.036 | 1.389 | 1.4919 | 1.4839 |

G. Filter the pulp with a 0.45 μm glass fiber syringe filter, and place the filtrate into the tube.
H. Set the spectrophotometer wavelength at 500 nm and the absorbance reading to zero using distilled water as reference.
I. Read and record the absorbance at 500 nm of the filtrate sample ($A_Y$).

Figure 2:
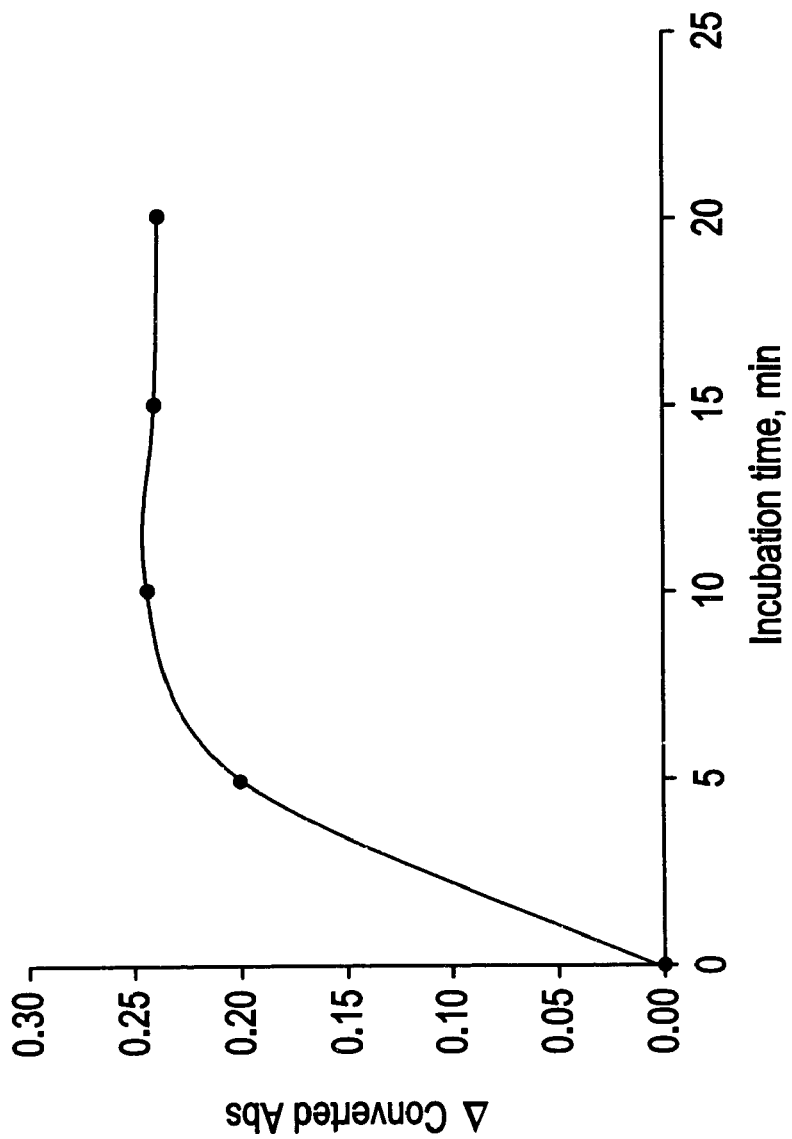
FIG. 2 is a graph of Δ converted absorbance of a pulp sample (from Decker Feed #1) treated with PC-B versus incubation time.

(II) Relating Absorbance to Triglyceride Concentration
A relative amount of depositable triglyceride would be determined from the difference between measured absor- The effect of the incubation time after adding PC-B on the converted absorbance using the Decker #1 sample is shown in Table 4 and FIG. 2. The sample weight was 2 g and the amount of PC-A added to each vial was 2.0 mL and the amount of PC-B was 0.5 mL. The triglyceride standard is 3000 mg/L of triolein. After 10 minutes, the converted absorbance reached a maximum and remained almost unchanged. Based on this test, the suggested incubation time was determined to be about 12 minutes. No triglycerides were added to these samples. Test "0" is the control sample, and Tests 1-5 are Decker Feed #1 samples.

TABLE 4

Effect of Incubation Time After Treating with PC-B

| Incub. time min | Test No. | TG sample mL | TG sample μg | Distilled water mL | $A_A$ abs | $A_{A+B}$ abs | Converted abs | Δ Converted abs |
|---|---|---|---|---|---|---|---|---|
|  | 0 | 0 | 0 | 3.000 | 0.021 | 0.030 | 0.000 |  |
| 0 | 1 | 0 | 0 | 1.000 | 0.034 | 0.030 | 0.0000 | 0.0000 |
| 5 | 2 | 0 | 0 | 1.000 | 0.034 | 0.211 | 0.1981 | 0.1981 |
| 10 | 3 | 0 | 0 | 1.000 | 0.034 | 0.252 | 0.2432 | 0.2432 |
| 15 | 4 | 0 | 0 | 1.000 | 0.034 | 0.249 | 0.2399 | 0.2399 |
| 20 | 5 | 0 | 0 | 1.000 | 0.034 | 0.248 | 0.2388 | 0.2388 |

Figure 3:
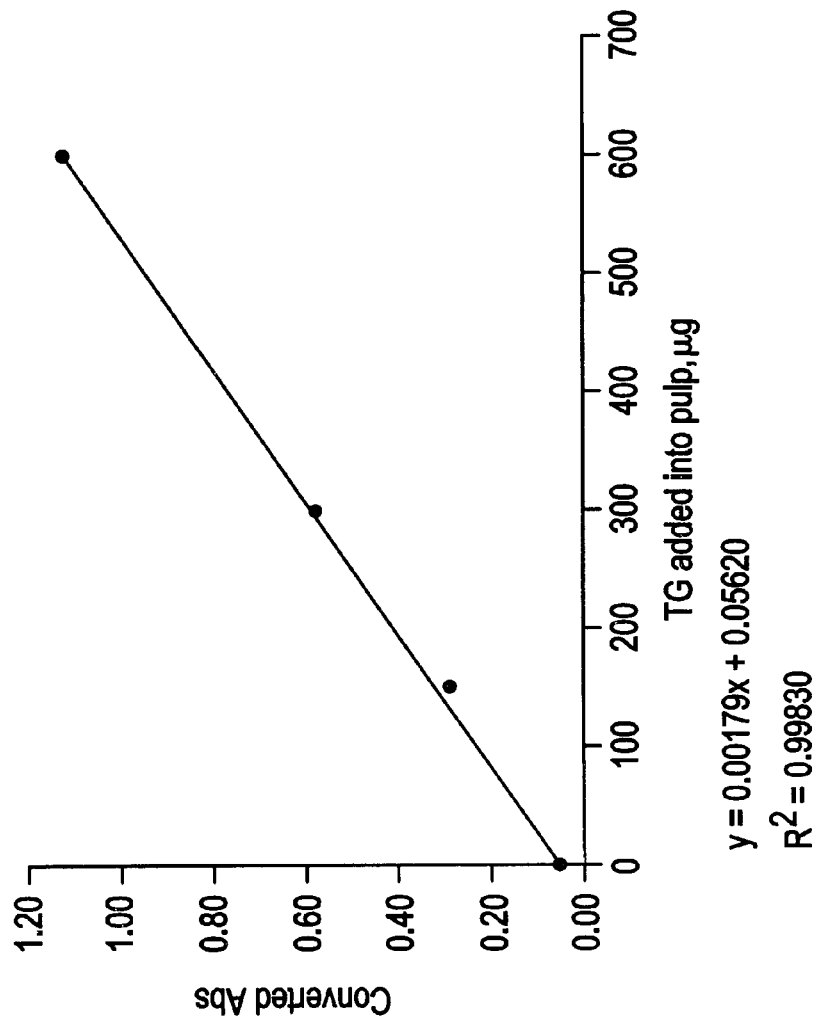
FIG. 3 is a graph of converted absorbance of a pulp sample (from paper machine #2 headbox) with added triglycerides versus amount of triglycerides added to the pulp sample.
Figure 4:
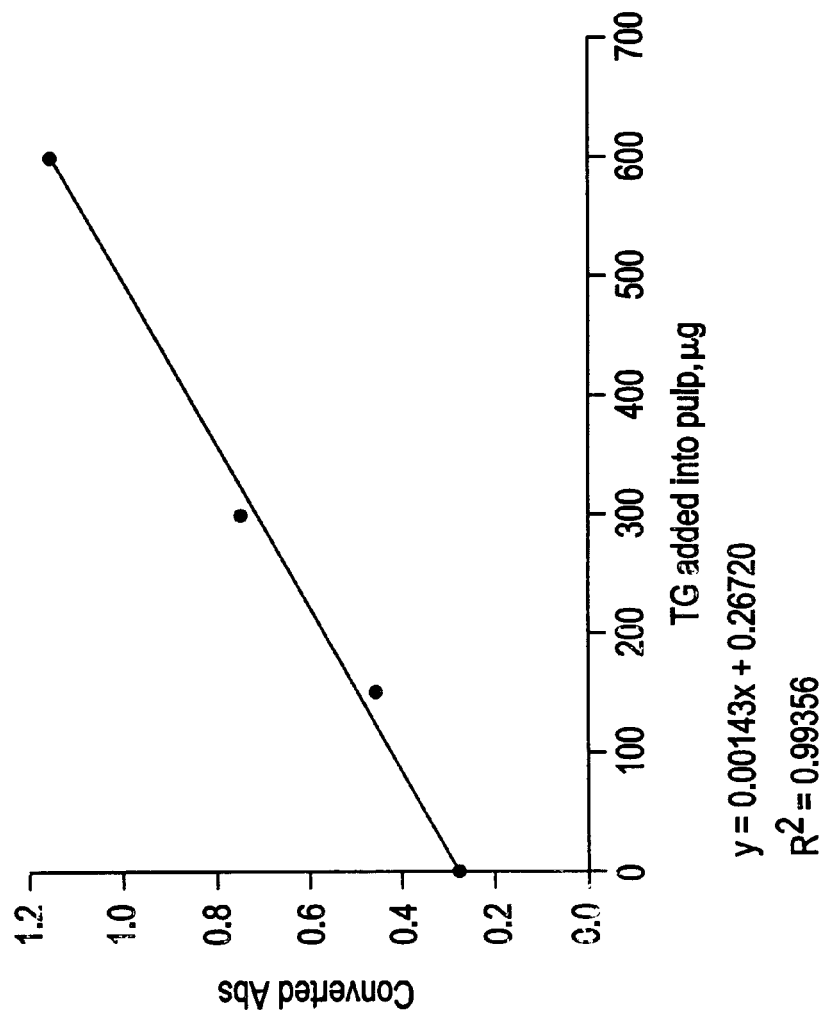
FIG. 4 is a graph of converted absorbance of a pulp sample (from low density chest #1) with added triglycerides versus amount of triglycerides added to the pulp sample.
Figure 5:
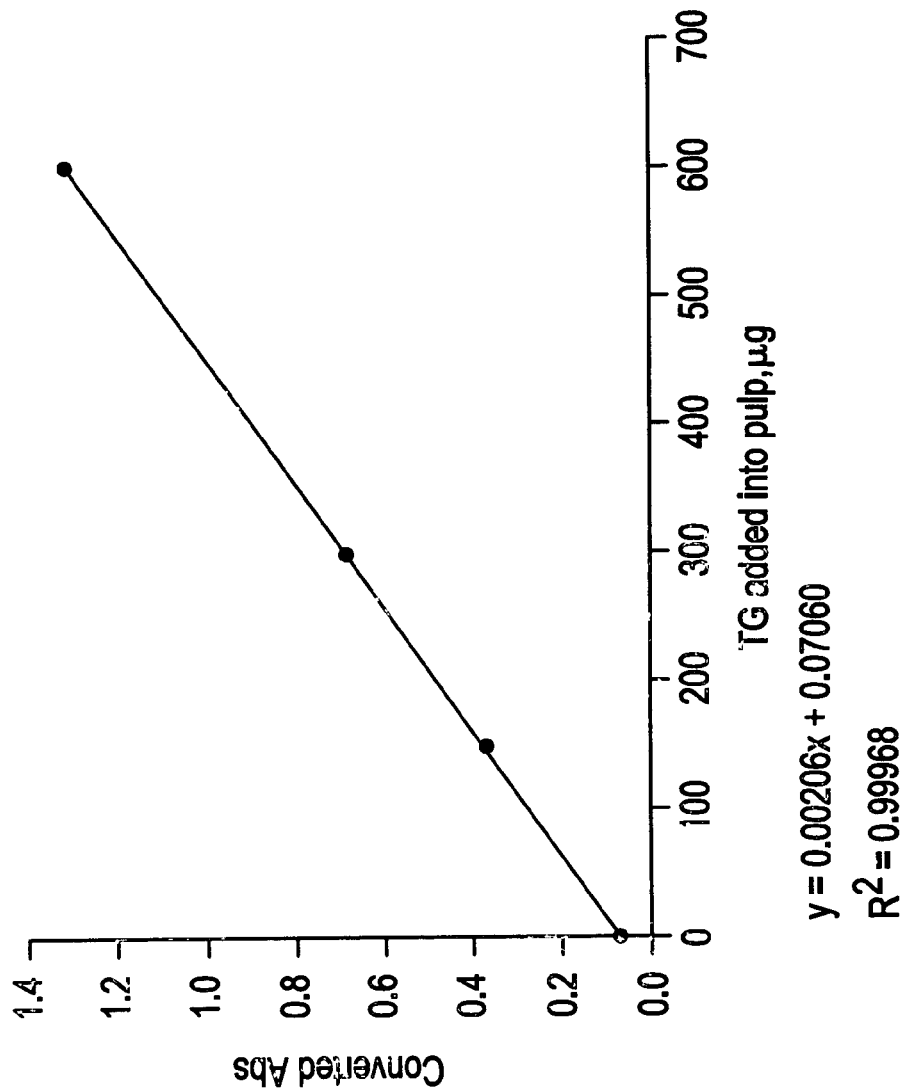
FIG. 5 is a graph of converted absorbance of a pulp sample (from paper machine #1 tray whitewater) with added triglycerides versus amount of triglycerides added to the pulp sample.
Figure 6:
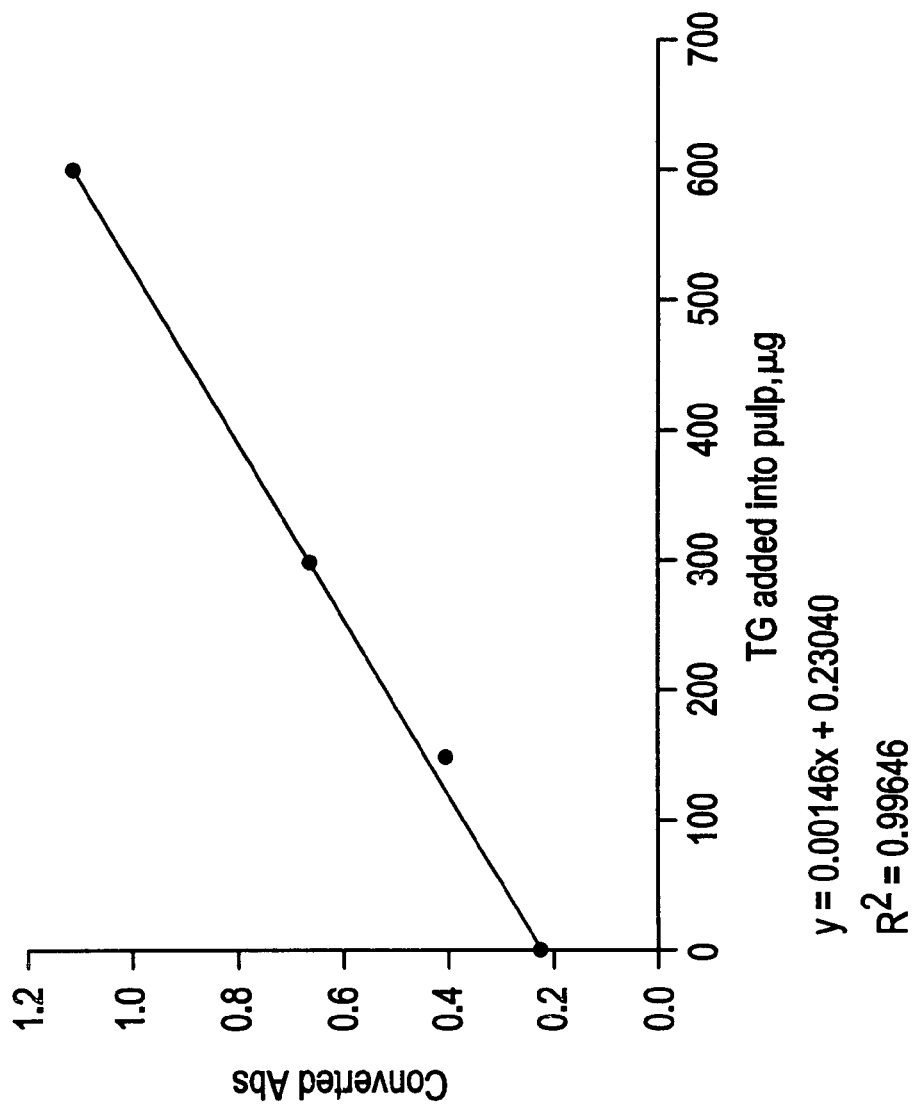
FIG. 6 is a graph of converted absorbance of a pulp sample (from Decker Feed #1) with added triglycerides versus amount of triglycerides added to the pulp sample.

Triglycerides were added to pulp and process water samples taken from various points in an actual, full scale paper mill, in order to assess industrial application of the test. The sample weight was 2 g and the amount of PC-A added to each vial was 2.0 mL and the amount of PC-B is 0.5 mL. The triglyceride standard is 3000 mg/L of triolein. These results from the following sample points are shown in the indicated tables and figures:

| Paper Machine #2 head box stock | Table 5 | FIG. 3 |
| Low Density Chest #1 stock | Table 6 | FIG. 4 |
| Paper Machine #1 tray white water | Table 7 | FIG. 5 |
| Decker Feed #1 stock | Table 8 | FIG. 6 |

TABLE 5

Results of adding triglycerides into paper machine #2 head box stock

| Test No. | Sample | Sample weight g | TG Sample mL | TG Sample μg | Distilled water mL | $A_A$ abs | $A_{A+B}$ abs | Converted abs | Δ Converted abs |
|---|---|---|---|---|---|---|---|---|---|
| 0 | Control | 0 | 0 | 0 | 3.000 | 0.025 | 0.026 | 0.000 |  |
| 1 | PM#2 Head Box | 2 | 0 | 0 | 1.000 | 0.067 | 0.112 | 0.0562 | 0.0000 |
| 2 | PM#2 Head Box | 2 | 0.05 | 150 | 0.950 | 0.079 | 0.338 | 0.2928 | 0.2366 |
| 3 | PM#2 Head Box | 2 | 0.1 | 300 | 0.900 | 0.088 | 0.613 | 0.5863 | 0.5301 |
| 4 | PM#2 Head Box | 2 | 0.2 | 600 | 0.800 | 0.091 | 1.117 | 1.1377 | 1.0815 |

TABLE 6

Results of adding triglycerides into low density chest #1 stock

| Test No. | Sample | Sample weight g | TG sample mL | TG sample μg | Distilled water mL | $A_A$ abs | $A_{A+B}$ abs | Converted abs | Δ Converted abs |
|---|---|---|---|---|---|---|---|---|---|
| 0 | Control | 0 | 0 | 0 | 3.000 | 0.025 | 0.026 | 0.000 |  |
| 1 | LD#1 avg. | 2 | 0 | 0 | 1.000 | 0.092 | 0.327 | 0.2672 | 0.0000 |
| 2 | LD#1 | 2 | 0.05 | 150 | 0.950 | 0.124 | 0.515 | 0.4425 | 0.1754 |
| 3 | LD#1 | 2 | 0.1 | 300 | 0.900 | 0.147 | 0.797 | 0.7297 | 0.4626 |
| 4 | LD#1 | 2 | 0.2 | 600 | 0.800 | 0.167 | 1.170 | 1.1200 | 0.8529 |

TABLE 7

Results of adding triglycerides into paper machine #1 tray whitewater

| Test No. | Sample | Sample weight g | TG sample mL | TG sample μg | Distilled water mL | $A_A$ abs | $A_{A+B}$ abs | Converted abs | Δ Converted abs |
|---|---|---|---|---|---|---|---|---|---|
| 0 | Control | 0 | 0 | 0 | 3.000 | 0.025 | 0.026 | 0.000 |  |
| 1 | PM#1 ww | 2 | 0 | 0 | 1.000 | 0.040 | 0.101 | 0.0706 | 0.0000 |
| 2 | PM#1 ww | 2 | 0.05 | 150 | 0.950 | 0.036 | 0.369 | 0.3699 | 0.2994 |

TABLE 7-continued

Results of adding triglycerides into paper machine #1 tray whitewater

| Test No. | Sample | Sample weight g | TG sample mL | TG sample μg | Distilled water mL | $A_A$ abs | $A_{A+B}$ abs | Converted abs | Δ Converted abs |
|---|---|---|---|---|---|---|---|---|---|
| 3 | PM#1 ww | 2 | 0.1 | 300 | 0.900 | 0.038 | 0.657 | 0.6847 | 0.6142 |
| 4 | PM#1 ww | 2 | 0.2 | 600 | 0.800 | 0.039 | 1.224 | 1.3074 | 1.2369 |

TABLE 8

Results of adding triglycerides into decker feed #1 stock

| Test No. | Sample | Sample weight g | TG sample mL | TG sample μg | Distilled water mL | $A_A$ abs | $a_{a+B}$ abs | Converted abs | Δ Converted abs |
|---|---|---|---|---|---|---|---|---|---|
| 0 | Control | 0 | 0 | 0 | 3.000 | 0.025 | 0.026 | 0.000 | |
| 1 | Decker#1 | 2 | 0 | 0 | 1.000 | 0.038 | 0.245 | 0.2304 | 0.0000 |
| 2 | Decker#1 | 2 | 0.05 | 150 | 0.950 | 0.069 | 0.436 | 0.4106 | 0.1802 |
| 3 | Decker#1 | 2 | 0.1 | 300 | 0.900 | 0.065 | 0.665 | 0.6665 | 0.4361 |
| 4 | Decker#1 | 2 | 0.2 | 600 | 0.800 | 0.075 | 1.081 | 1.1141 | 0.8837 |

FIGS. 3–6 demonstrate that the absorbance of pulp plus added triglycerides have a linear relationship with added triglycerides when the added triglycerides are less than or equal to 600 μg.

It has been found that the pulp of each tree species and each mill's water has a different relationship between the absorbance figures and the resident TG. Controlled testing of each tree species and mill water can be used to calibrate this relationship. Table 9 illustrates the reproducibility of the triglyceride results analyzed at one mill by this new method. The results show that the reproducibility of the new method is very high. The relative error for analyzing the pulp samples is generally below 5%.

TABLE 9

Reproducibility of the triglyceride analysis method

| Sample | Triglycerides ppm |
|---|---|
| Decker #1 | 82.4 |
| Decker #1 | 79.7 |
| Decker #1 | 78.2 |
| Mean(ppm) | 80.1 |
| Standard Deviation | 2.13 |
| Coefficient of variation (%) | 2.7 |
| Number of assay | 3 |
| Low Density Chest #1 | 196.4 |
| Low Density Chest #1 | 210.9 |
| Low Density Chest #1 | 203.1 |
| Low Density Chest #1 | 217.9 |
| Low Density Chest #1 | 195.3 |
| Mean(ppm) | 204.7 |
| Standard Deviation | 9.65 |
| Coefficient of variation (%) | 4.7 |
| Number of assay | 5 |
| Low Density Chest #2 | 274.3 |
| Low Density Chest #2 | 269.0 |
| Mean(ppm) | 271.7 |
| Standard Deviation | 3.80 |
| Coefficient of variation (%) | 1.4 |
| Number of assay | 2 |
| Paper Machine #1 Headbox | 29.3 |
| Paper Machine #1 Headbox | 29.4 |
| Paper Machine #1 Headbox | 33.4 |

TABLE 9-continued

Reproducibility of the triglyceride analysis method

| Sample | Triglycerides ppm |
|---|---|
| Mean(ppm) | 30.7 |
| Standard Deviation | 2.34 |
| Coefficient of variation (%) | 7.6 |
| Number of assay | 2 |

Conclusions

An enzymatic calorimetric triglyceride analysis has been developed, which is quick (e.g., ~20 min. to complete) and has high reproducibility and small relative error (e.g., <5 to 10%). Importantly, no volatile organic solvent was needed to perform the triglyceride analysis.

EXAMPLE 4

The Effect of Hydrogen Peroxide and Hydrosulfite on Triglyceride Assay Methods

An experiment was conducted to determine how the assay for pulp without residual hydrogen peroxide or hydrosulfite and the assay for pulp containing hydrogen peroxide or hydrosulfite are affected by the presence of hydrogen peroxide and hydrosulfite, since these substances are present in many pulp samples. The experiments using the assay for pulp without residual hydrogen peroxide or hydrosulfite, detailed below, showed that hydrogen peroxide interferes with the reaction sequence since it is an intermediate product and reactant in the reaction sequence for this assay. Hydrosulfite also interferes with this assay since hydrosulfite acts as a reducing agent for many dyes and the final end product for this assay is a dye such as quinoneimine dye. The results of the experiments with the assay for pulp containing hydrogen peroxide or hydrosulfite show that hydrogen peroxide does not interfere with the reaction sequence and therefore has no affect on the assay method. Hydrosulfite does interfere with the assay for pulp containing hydrogen peroxide or hydrosulfite, as two different dyes are involved in the reaction sequence: INT and formazan. To overcome the limitations of the assay for pulp containing hydrogen peroxide or hydrosulfite, experiments were performed to determine if the hydrosulfite could be reacted with hydrogen peroxide before the assay was executed.

Procedure

The experiment consisted of three determinations: (i) how the assay for pulp without residual hydrogen peroxide or hydrosulfite was affected with varying concentrations of peroxide and hydrosulfite using 50 ppm glycerol and 100 ppm triolein as substrates; (ii) how the assay for pulp containing hydrogen peroxide or hydrosulfite was affected with varying concentrations of peroxide and hydrosulfite using 50 ppm glycerol and 100 ppm triolein as substrates; and (iii) under what conditions could 1000 ppm of hydrosulfite be reacted with peroxide such that the assay for pulp containing hydrogen peroxide or hydrosulfite could be used to assay for triglycerides.

Experiments were performed using two different assay methods with 100 ppm triolein and 50 ppm glycerol as substrates at the following varying concentrations of hydrogen peroxide and hydrosulfite: 0, 50, 100, 200, 400, and 1000 ppm. A control blank that did not contain any substrate was used for each experiment.

Results and Discussion

PC-A along with the addition of PC-B was used to assay for the presence of triglycerides. The enzymatic reactions involved in this one embodiment of the assay were as follows: The triglycerides were reduced to glycerol and fatty acids by a lipase. The glycerol was reacted to form glycerol-1-phospate which reacts with oxygen to form peroxide. The peroxide reacted with 4-aminoantipyrine and ESPA to form quinoneimine dye and water. From this series of reactions the concentration of quinoneimine dye formed as the final product was directly proportional to the concentration of triglycerides initially present in the sample.

Hydrogen peroxide is a reaction product in the third reaction and a reactant in the fourth reaction so the amount of hydrogen peroxide formed is proportional to the initial concentration of triglycerides. However, there is a problem with this reaction scheme if hydrogen peroxide is already present in the pulp sample, because the hydrogen peroxide can start to react with the 4-aminoantipyrine and ESPA and form the quinoneimine dye, or the reverse of the third reaction can occur when peroxide is present in excess.

Figure 7:
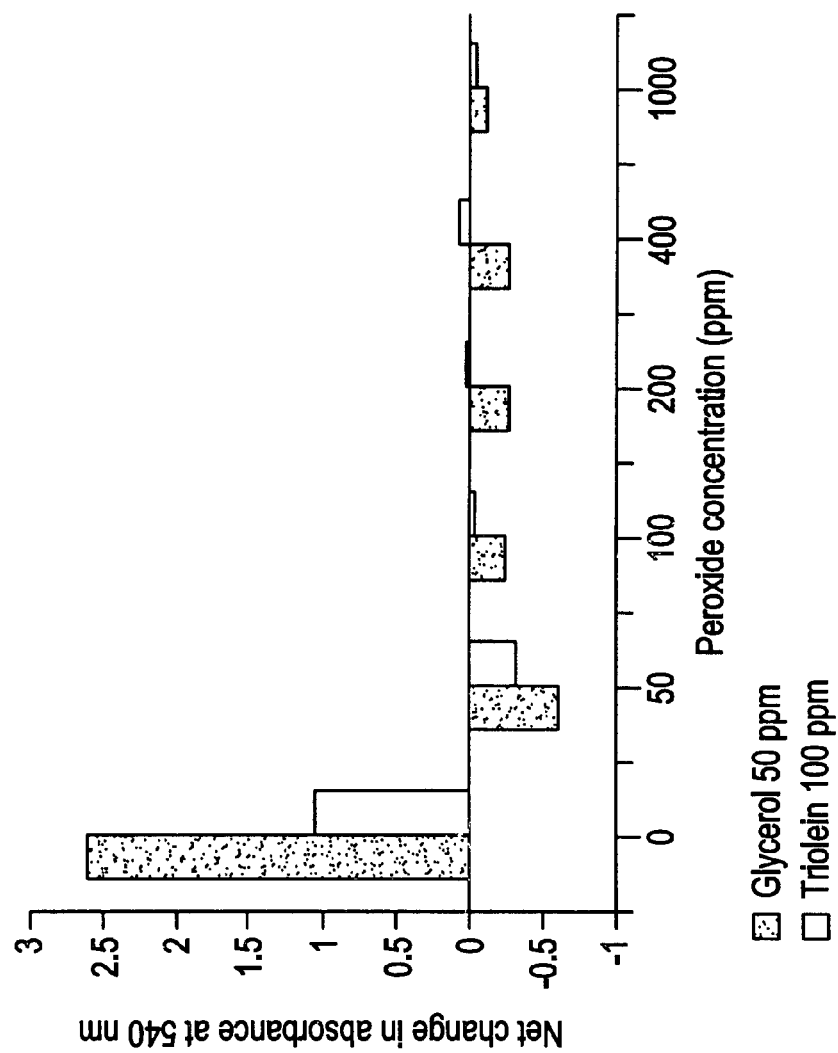
FIG. 7 is a graph of net change in absorbance at 540 nm versus peroxide concentration, showing the effect of peroxide concentration on the assay for pulp without residual hydrogen peroxide or hydrosulfite (PC-A and PC-B), using 50 ppm glycerol or 100 ppm triolein.

The effect of peroxide on the assay for pulp without residual hydrogen peroxide or hydrosulfite is shown in Table 10 and FIG. 7. The results show that without the addition of either glycerol or triolein, the peroxide reacts to form a quinoneimine dye at low peroxide concentrations, and the amount of dye produced decreases as the concentration is increased. The amount of quinoneimine dye decreases as the peroxide level increases because hydrogen peroxide is present in excess, which causes the third reaction to reverse itself. These same trends were evident even with the addition of 100 ppm of triolein or 50 ppm of glycerol to the PC-A Reagent before the addition of peroxide. FIG. 7 shows the change in absorbance (final absorbance—blank) as a function of peroxide concentration. The net change for all peroxide concentrations is close to zero. If hydrogen peroxide is initially present in a pulp sample, it likely may not be possible to accurately determine the concentration of triglycerides using this method.

TABLE 10

Effect of peroxide on the assay for pulp without residual hydrogen peroxide or hydrosulfite

| Peroxide Concentration (ppm) | Blank Absorbance 540 nm | Glycerol 50 ppm Absorbance 540 nm | Triolein 100 ppm Absorbance 540 nm |
|---|---|---|---|
| 0 | 0.0535 | 2.6469 | 1.0942 |
| 50 | 2.9166 | 2.3206 | 2.6096 |
| 100 | 1.7511 | 1.5177 | 1.7357 |
| 200 | 1.3324 | 1.0922 | 1.3567 |
| 400 | 0.9492 | 0.7091 | 1.0311 |
| 1000 | 0.5420 | 0.4589 | 0.5263 |

Figure 8:
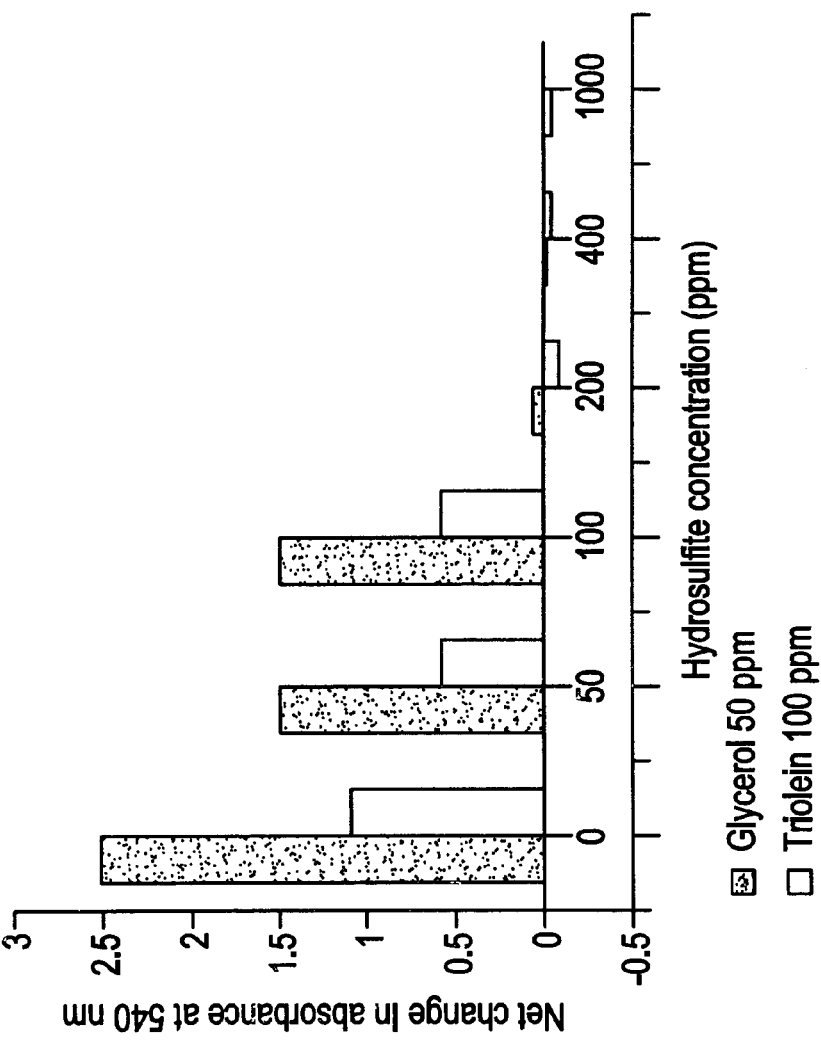
FIG. 8 is a graph of net change in absorbance at 540 nm versus hydrosulfite concentration, showing the effect of hydrosulfite concentration on the assay for pulp without residual hydrogen peroxide or hydrosulfite (PC-A and PC-B), using 50 ppm glycerol or 100 ppm triolein.

It is known that hydrosulfite can act as a reducing agent for many dyes, as it effectively acts to bleach the dye. The effect of hydrosulfite on the assay for pulp without residual hydrogen peroxide or hydrosulfite is shown in Table 11 and FIG. 8. The results show that without the addition of either glycerol or triolein, the series of reactions does not occur and there is no color change. With the addition of 100 ppm of triolein or 50 ppm of glycerol to the PC-A Reagent before the addition of hydrosulfite, the hydrosulfite reduces the dye such that the absorbance decreases as the concentration of hydrosulfite increases. FIG. 8 shows the change in absorbance (final absorbance—blank) as a function of hydrosulfite concentration. The net change in absorbance is close to zero for hydrosulfite concentrations above 100 ppm. At concentrations below 100 ppm, the net change in absorbance is lower than the 0 ppm control, but it still might be possible to use this method. If hydrosulfite is initially present in a pulp sample with a concentration in excess of 100 ppm, it may not be possible to accurately determine the concentration of triglycerides using this method.

TABLE 11

Effect of hydrosulfite on the assay for pulp without residual hydrogen peroxide or hydrosulfite

| Peroxide Concentration (ppm) | Blank Absorbance 540 nm | Glycerol 50 ppm Absorbance 540 nm | Triolein 100 ppm Absorbance 540 nm |
|---|---|---|---|
| 0 | 0.0848 | 2.5643 | 1.1661 |
| 50 | 0.0981 | 1.5911 | 0.6557 |
| 100 | 0.0076 | 1.4768 | 0.5799 |
| 200 | 0.0977 | 0.1537 | 0.0248 |
| 400 | 0.0275 | 0.0301 | 0.0082 |
| 1000 | 0.0451 | 0.0266 | 0.0554 |

PC-Y along with the addition of PC-Z was used to assay for the presence of triglycerides. The enzymatic reactions involved in this assay were as follows: The triglycerides were reduced to glycerol and fatty acids by a lipase. The glycerol was reacted to form glycerol-1-phospate which reacts with NAD to form NADH. The NAD reacted with INT to form quinoneimine dye and NAD. From this series of reactions, the concentration of quinoneimine dye formed as the final product was directly proportional to the concentration of triglycerides initially present in the sample. The advantage of this method is that hydrogen peroxide is not present in the reaction scheme. In theory, if hydrogen peroxide is initially present in the pulp sample, it should not affect the reaction sequence.

Figure 9:
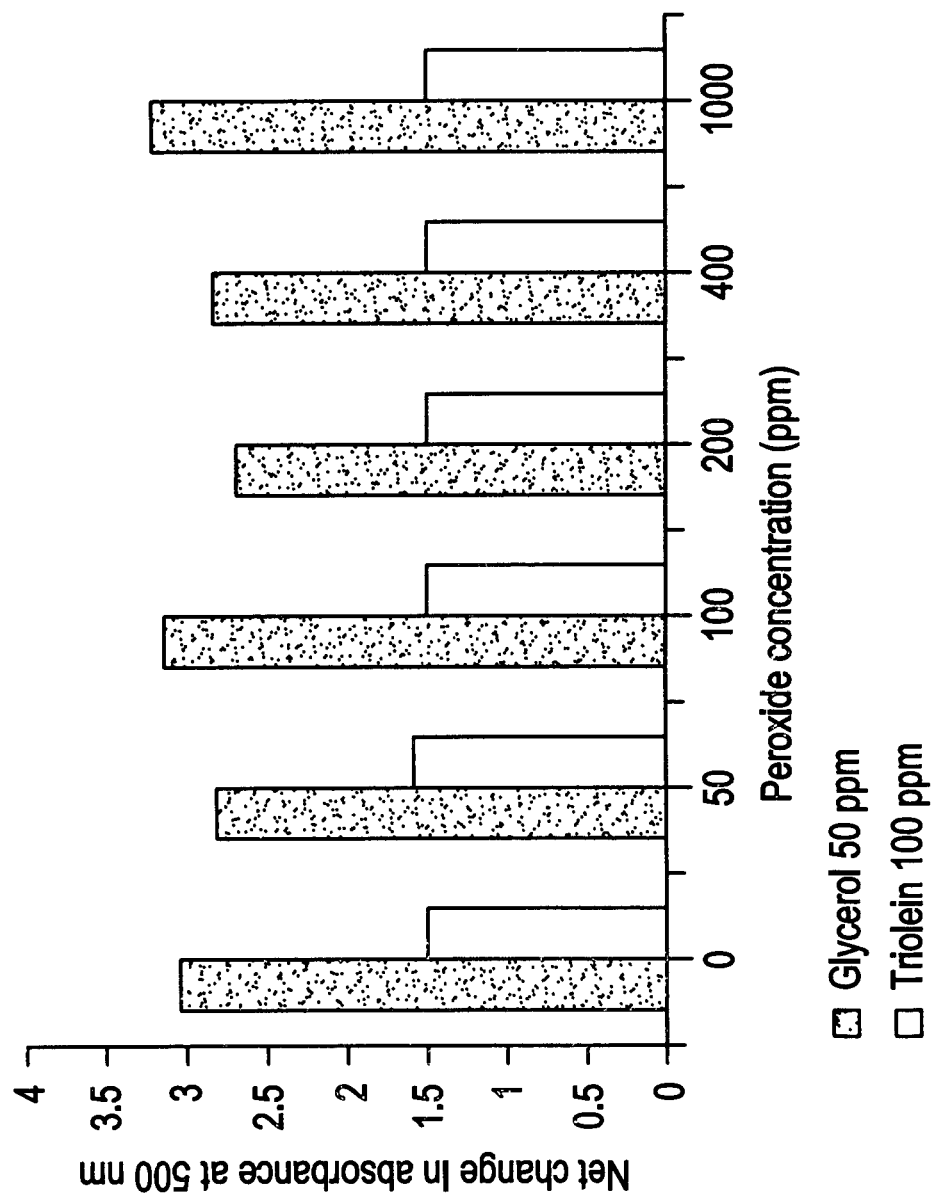
FIG. 9 is a graph of net change in absorbance at 500 nm versus peroxide concentration, showing the effect of peroxide concentration on the assay for pulp containing hydrogen peroxide (PC-Y and PC-Z), using 50 ppm glycerol or 100 ppm triolein.

The effect of peroxide on the assay for pulp containing hydrogen peroxide is shown in Table 12 and FIG. 9. The results show that without the addition of either glycerol or triolein, the series of reactions does not occur and there is no color change. With the addition of either glycerol or triolein, the series of reactions occurs and is not affected by the addition of peroxide. FIG. 9 shows the change in absorbance (final absorbance—blank) as a function of peroxide concentration. The net change for all peroxide concentrations stays relatively constant from 0 to 1000 ppm. If hydrogen peroxide is initially present in a pulp sample, it is possible to accurately determine the concentration of triglycerides using this method.

TABLE 12

Effect of peroxide on the assay for pulp containing hydrogen peroxide

| Peroxide Concentration (ppm) | Blank Absorbance 500 nm | Glycerol 50 ppm Absorbance 500 nm | Triolein 100 ppm Absorbance 500 nm |
|---|---|---|---|
| 0 | 0.0951 | 3.1230 | 1.5927 |
| 50 | 0.0942 | 2.8973 | 1.6696 |
| 100 | 0.1349 | 3.2614 | 1.6273 |
| 200 | 0.1366 | 2.8027 | 1.6427 |
| 400 | 0.1389 | 2.9470 | 1.6100 |
| 1000 | 0.1359 | 3.3193 | 1.6427 |

Figure 10:
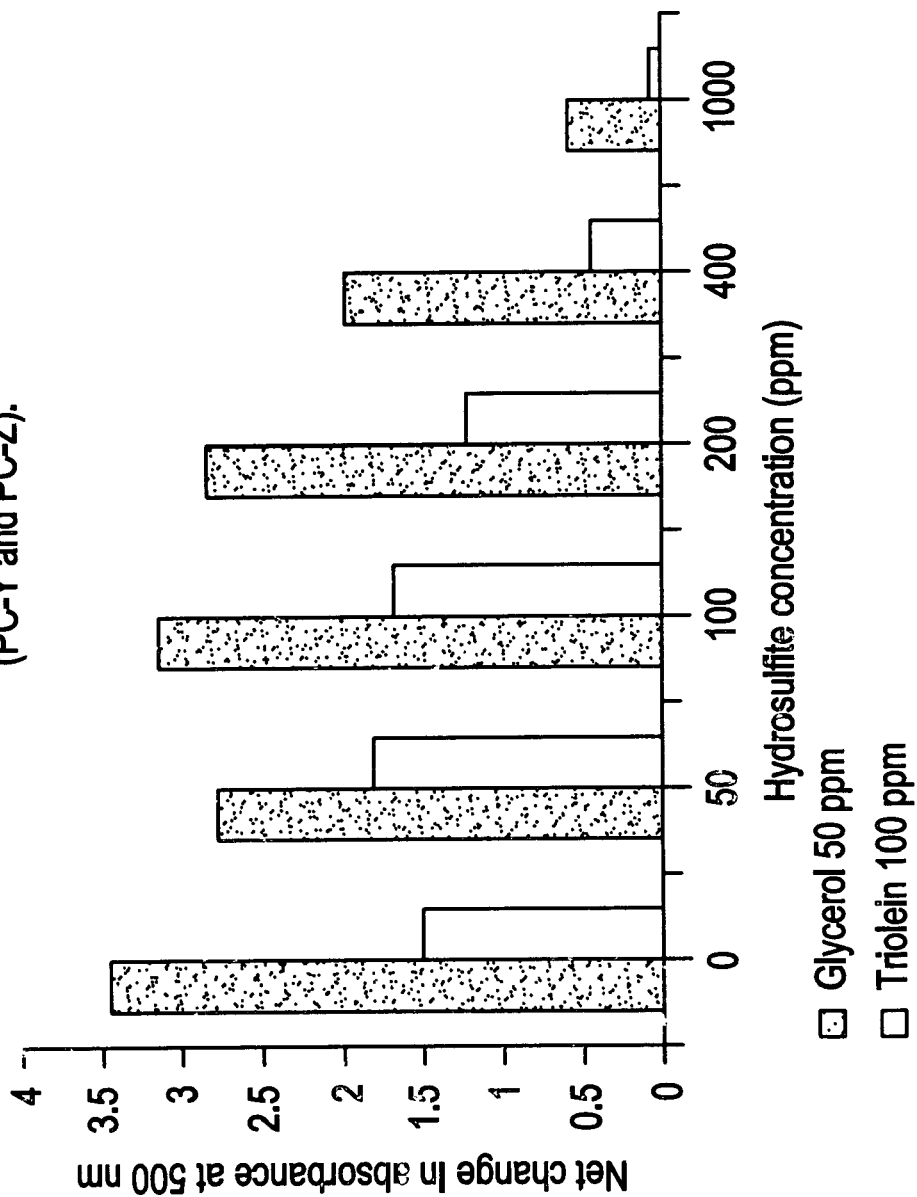
FIG. 10 is a graph of net change in absorbance at 500 nm versus hydrosulfite concentration, showing the effect of hydrosulfite concentration on the assay for pulp containing hydrosulfite (PC-Y and PC-Z), using 50 ppm glycerol or 100 ppm triolein.

The effect of hydrosulfite on the assay for pulp containing hydrosulfite is shown in Table 13 and FIG. 10. The results show that without the addition of either glycerol or triolein, the hydrosulfite reacts to reduce the INT dye that is present in the PC-Y reagent formula and produces a color change. As the concentration of hydrosulfite increases, the absorbance of the blank increases. With the addition of 100 ppm of triolein or 50 ppm of glycerol to the Reagent A before the addition of hydrosulfite, the hydrosulfite reduces the formazan dye product such that the absorbance decreases as the concentration of hydrosulfite increases. FIG. 10 shows the change in absorbance (final absorbance—blank) as a function of hydrosulfite concentration. The net change in absorbance decreases as the concentration of hydrosulfite increases. It is still possible to use this method at low hydrosulfite concentrations, around 100 ppm or less.

TABLE 13

Effect of hydrosulfite on the assay for pulp containing hydrosulfite

| Hydrosulfite Concentration (ppm) | Blank Absorbance 500 nm | Glycerol 50 ppm Absorbance 500 nm | Triolein 100 ppm Absorbance 500nm |
|---|---|---|---|
| 0 | 0.1355 | 3.5701 | 1.6069 |
| 50 | 0.3215 | 3.0930 | 2.1249 |
| 100 | 0.4086 | 3.5191 | 2.0858 |
| 200 | 0.5266 | 3.3593 | 1.7457 |
| 400 | 0.6873 | 2.6537 | 1.1205 |
| 1000 | 0.9937 | 1.5784 | 0.9974 |

Figure 11:
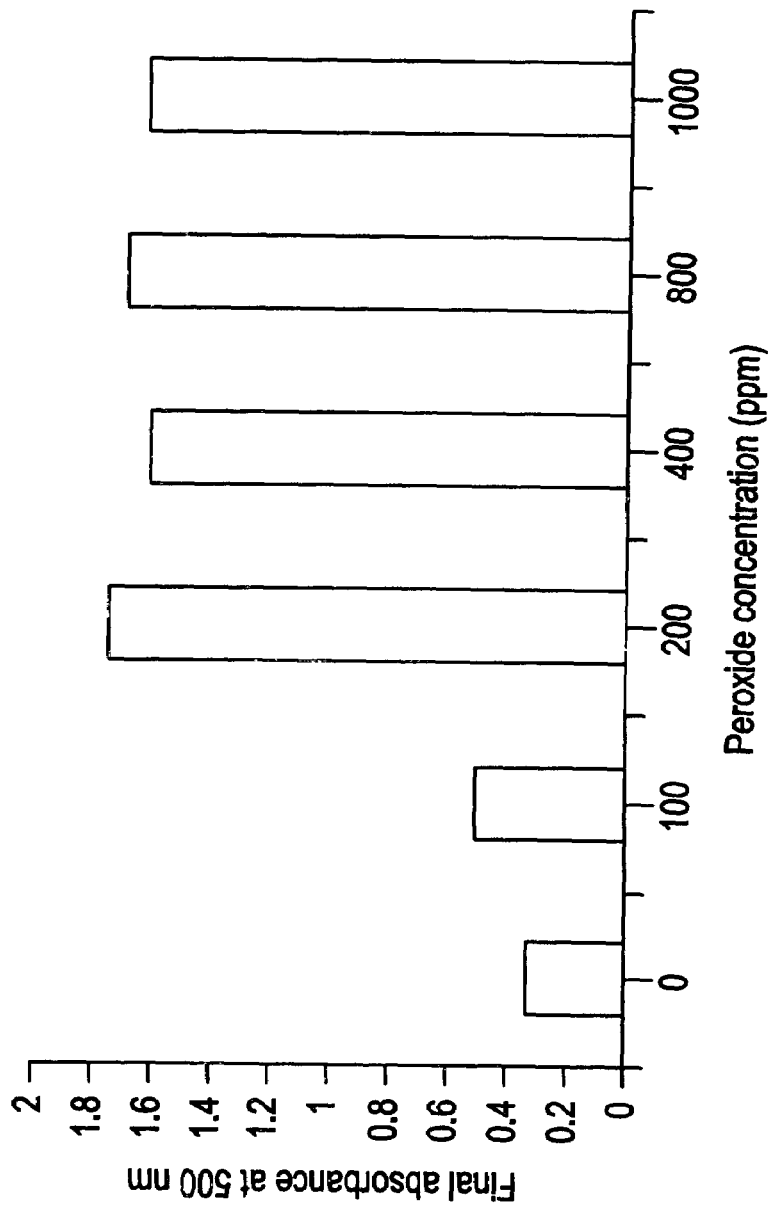
FIG. 11 is a graph of final absorbance at 500 nm versus peroxide concentration, showing the effect of peroxide on a 100 ppm triolein sample with 1000 ppm hydrosulfite using the assay for pulp containing hydrogen peroxide or hydrosulfite.

Since the assay for pulp containing hydrogen peroxide or hydrosulfite reaction scheme is affected by hydrosulfite, but not by hydrogen peroxide, it should be possible to react the hydrosulfite with hydrogen peroxide before initiating the assay such that the assay is not affected by the hydrosulfite. The results are shown in Table 14 and FIG. 11. For this experiment, the hydrosulfite concentration was held constant at 1000 ppm and various concentrations of peroxide were added before the PC-Y Reagent was added. Triolein was used as the substrate at a concentration of 100 ppm. The results show that as the concentration of peroxide increases, the absorbance increases up to 200 ppm and then levels off. These results indicate that it might be possible to use this assay for pulp containing hydrogen peroxide or hydrosulfite to determine the triglyceride concentration in a pulp sample that contains hydrogen sulfite if hydrogen peroxide is first added to react with the hydrogen sulfite.

TABLE 14

Effect of peroxide on the assay for pulp containing hydrogen peroxide or hydrosulfite with 100 ppm triolein and 1000 ppm hydrosulfite

| Peroxide Concentration (ppm) | Final Absorbance 500 nm |
|---|---|
| 0 | 0.3391 |
| 100 | 0.5060 |
| 200 | 1.7361 |
| 400 | 1.6094 |
| 800 | 1.6792 |
| 1000 | 1.6175 |

Conclusions

The results show that the assay for pulp containing hydrogen peroxide or hydrosulfite can be used to assay for triglycerides if the hydrosulfite initially present is reacted with hydrogen peroxide. A level of 200 ppm peroxide could be effectively reacted with 1000 ppm of hydrosulfite. The assay for pulp containing hydrogen peroxide or hydrosulfite can be used to assay for triglycerides even with the presence of hydrogen peroxide in the sample, since hydrogen peroxide is not involved in the reaction sequence. If hydrosulfite is present in the sample, it is necessary to add an appropriate amount of peroxide to the sample before performing the assay for pulp containing hydrogen peroxide or hydrosulfite.

Those skilled in the art will recognize, or be able to ascertain using no more than routine experimentation, many equivalents to the specific embodiments of the invention described herein. The references cited herein are hereby incorporated by reference.

We claim:

1. A method for determining the depositable triglycerides content in a wood pulp sample, the method comprising:
   (a) determining the amount of glycerol or fatty acids in a wood pulp sample;
   (b) reacting the wood pulp sample with an effective amount of a lipolytic enzyme for a sufficient time to form glycerol and fatty acids; and
   (c) determining the difference in the amount of glycerol or fatty acids in the wood pulp sample before and after reaction with the lipolytic enzyme.

2. The method of claim 1, wherein the lipolytic enzyme comprises a lipase.

3. The method of claim 1, wherein the lipolytic enzyme comprises a non-lipase enzyme.

4. The method of claim 3, wherein the non-lipase enzyme comprises a carboxylesterase.

5. The method of claim 1, wherein the difference between the amounts of glycerol present in the wood pulp sample before and after treatment with the lipolycic enzyme is determined.

6. The method of claim 5, wherein the lipolytic enzyme comprises a lipase.

7. The method of claim 5, comprising reacting glycerol in one or more reactions to form a measurable species and determining the concentration of the measurable species present in the wood pulp sample before and after treatment with the lipolytic enzyme.

8. The method of claim 7, wherein the concentration of the measurable species is determined by measuring a property selected from the group consisting of concentration of an electrochemical species, spectrometric characteristics, and chromatographic characteristics.

9. The method of claim 7, wherein the measurable species is a colored substrate and the measurement is obtained spectrophotometrically.

10. The method of claim 7, wherein the glycerol is phosphorylated in the one or more reactions.

11. The method of claim 10, wherein the glycerol is converted to glycerol-1-phosphate or glycerol-3-phosphate.

12. The method of claim 11, wherein the glycerol-1-phosphate or glycerol-3-phosphate is enzymatically oxidized with an electron acceptor.

13. The method of claim 12, wherein the glycerol-1-phosphate or glycerol-3-phosphate is reacted with oxygen ($O_2$) to form dihydroxyacetone phosphate and hydrogen peroxide.

14. The method of claim 13, wherein the hydrogen peroxide is reacted with a dye precursor to produce a measurable color change.

15. The method of claim 14, wherein the reaction of the hydrogen peroxide with the dye precursor produces a quinoneimine dye.

16. The method of claim 15, wherein peroxidase catalyzes the oxidation of a chromogen of peroxidase in the presence of hydrogen peroxide.

17. The method of claim 16, wherein the hydrogen peroxide reaction is reacted with 4-aminoantipyrine and a compound selected from the group consisting of sodium-N-ethyl-N-(3-sulfopropyl) m-anisidine (ESPA), p-chlorophenol, and 3,5-dichloro-2-hydoxybenzene sulfonate (DHBS), in the presence of a peroxidase.

18. The method of claim 16, wherein the chromogen of peroxidase is selected from the group consisting of monoamines, diamines, phenols, polyphenols, aromatic acids, leuco dyes, and colored dyes.

19. The method of claim 12, wherein the glycerol-1-phosphate or glycerol-3-phosphate is reacted with nicotinamide adenine dinucleotide (NAD) to form reduced nicotinamide adenine dinucleotide (NADH).

20. The method of claim 19, wherein the NADH is reacted with a dye precursor to produce a measurable color change.

21. The method of claim 20, wherein the reaction of the NADH with the dye precursor produces formazan dye.

22. The method of claim 21, wherein the NADH is reacted with 2-(p-iodophenyl)-3-p-nitrophenyl-5-phenyltrazolium chloride (INT) or with nitro blue tetrazolium (NBT), in the presence of a diaphorase.

23. The method of claim 7, wherein the glycerol is enzymatically reacted with adenosine triphosphate.

24. The method of claim 23, wherein the glycerol is reacted with adenosine triphosphate in the presence of a glycerol kinase to produce adenosine-5'-diphosphate (ADP).

25. The method of claim 24, wherein the ADP is then reacted with phosphoenol pyruvate to produce pyruvate.

26. The method of claim 25, wherein the pyruvate is then reacted with a dye precursor to produce a measurable color change.

27. The method of claim 26, wherein the reaction of the pyruvate with the dye precursor produces NAD.

28. The method of claim 26, wherein the pyruvate is reacted with NADH in the presence of a lactate dehydrogenase.

29. The method of claim 12, wherein the glycerol-1-phosphate is reacted with oxygen in the presence of glycerol phosphate oxidase to produce dihydroxyacetone phosphate and hydrogen peroxide, and the peroxide is then reacted with 4-aminoantipyrine and sodium-N-ethyl-N-(3-sulfopropyl) m-anisidine to produce quinoneimine dye.

30. The method of claim 12, wherein the glycerol-1-phosphate or glycerol-3-phosphate is reacted with oxygen in the presence of glycerol phosphate oxidase to produce dihydroxyacetone phosphate and hydrogen peroxide, and the peroxide is then reacted with 4-aminoantipyrine and 3,5-Dichloro-2-hydoxybenzene sulfonate (DHBS) to produce quinoneimine dye.

31. The method of claim 12, wherein the glycerol-1-phosphate is reacted with oxygen in the presence of glycerol phosphate oxidase to produce dihydroxyacetone phosphate and hydrogen peroxide, and the peroxide is then reacted with 4-aminoantipyrine and p-chlorophenol to produce quinoneimine dye.

32. The method of claim 12, wherein the glycerol-1-phosphate is reacted in the presence of glycerol-1-phosphate dehydrogenase with nicotinamide adenine dinucleotide to form dihyroxyacetone phosphate and NADH, and the NADH is then reacted in the presence of diaphorase with 2-(p-iodophenyl)-3-p-nitrophenyl-5-phenyltrazolium chloride (INT) to produce formazan dye and nicotinamide adenine dinucleotide (NAD).

33. The method of claim 12, wherein the glycerol-1-phosphate is reacted in the presence of glycerol-1-phosphate dehydrogenase with nicotinamide adenine dinucleotide to form dihydroxyacetone phosphate and NADH, and the NADH is then reacted in the presence of diaphorase with nitro blue tetrazolium (NBT) to produce formazan dye.

34. The method of claim 7, wherein the glycerol is reacted with ATP in the presence of glycerol kinase to produce ADP, the ADP is then reacted with phosphoenol pyruvate in the presence of pyruvate kinase to produce pyruvate and ATP, and then the pyruvate is reacted with NADH in the presence of lactate dehydrogenase to produce lactate and NAD.

35. The method of claim 14, wherein the wood pulp sample comprises less than about 100 ppm hydrogen peroxide or hydrosulfite, before reacting with the lipase.

36. The method of claim 20, wherein the wood pulp sample comprises more than about 100 ppm hydrogen peroxide or hydrosulfite, before reacting with the lipase.

37. The method of claim 1, further comprising adding an effective amount of a fiber surface modifier to the wood pulp sample to liberate at least a portion of the depositable triglycerides from cellulosic fibers of the wood pulp sample.

38. The method of claim 37, wherein the fiber surface modifier comprises an enzyme selected from the group consisting of cellulases, hemi-cellulases, xylanases, ligninases, pectinases, proteases, manninases, glucomanninases, arabinonases, amylases, and combinations thereof.

39. The method of claim 37, wherein the fiber surface modifier comprises a surfactant, a polymeric additive, a polyelectrolyte, or a combination thereof.

40. The method of claim 1, wherein the lipolytic enzyme is included in a dry test strip for reaction with the depositable triglycerides.

41. The method of claim 1, comprising reacting the fatty acids in one or more reactions to form a mensurable suedes and determining the concentration of the measurable species present in the wood pulp sample before and after treatment with the lipolytic enzyme.

42. The method of claim 41, wherein the concentration of the measurable species is determined by measuring a property selected from the group consisting of concentration of an electrochemical species, spectrometric characteristics, and chromatographic characteristics.

43. The method of claim 42, wherein the chromatographic characteristics are obtained from a test selected from the group consisting of high performance liquid chromatography, gas chromatography, thin layer chromatography, nuclear magnetic resonance imaging, mass spectroscopy, flame ionization detection, and gas-liquid chromatography.

44. The method of claim 1 conducted on-line.

45. The method of claim 1 conducted in a batch process.

46. The method of claim 1 conducted in a continuous or semi-continuous process.

47. The method of claim 1, comprising determining the difference between the amount of glycerol or fatty acids present in the wood pulp sample electrochemically.

48. The method of claim 47, wherein an electrochemical species is oxygen.

49. The method of claim 47, wherein an electrochemical species is hydrogen peroxide.

50. The method of claim 47, wherein the determination of the change in concentration of an electrochemical species comprises the use of an electrode assembly.

51. The method of claim 50, wherein the electrode assembly comprises an oxygen-sensing electrode.

52. The method of claim 50, wherein the electrode assembly comprises an ion-selective electrode.

53. The method of claim 50, wherein the electrode assembly measures a change in an electrical current.

54. The method of claim 53, wherein the change in electrical current is caused by metal-catalyzed reduction of hydrogen peroxide.

55. The method of claim 47, wherein the change in concentration of an electrochemical species is determined potentiometrically.

56. The method of claim 1, wherein a first series of reactions is performed on a first portion of the wood pulp sample and a second series of reactions is performed on a second portion of the wood pulp sample, said first series comprising: (i) reacting the depositable triglycerides in the presence of a lipase to form glycerol and fatty acids; (ii) reacting the free glycerol and glycerol of step (i) in the presence of a first enzyme to form a first quantity of glycerol-1-phosphate; and (iii) reacting the first quantity of glycerol-1-phosphate in the presence of one or more enzymes in one or more reactions with a dye precursor compound to yield a colored substrate in a first amount which is directly and molecularly proportional to the first quantity of glycerol-1-phosphate; and said second series comprising: (i) reacting the free glycerol in the presence of a second enzyme to form a second quantity of glycerol-1-phosphate; and (ii) reacting the second quantity of glycerol-1-phosphate in the presence of one or more enzymes in one or more reactions with a dye precursor compound to yield a colored substrate in a second amount which is directly and molecularly proportional tote second quantity of glycerol-1-phosphate; wherein the amount of surface triglycerides present in the sample of wood pulp is determined by comparing the first amount of colored substrate with the second amount of colored substrate.

57. A method for enhancing pitch control in a pulp and paper mill comprising: (a) obtaining one or more wood pulp samples from a sampling point in a pulp and paper mill; (b) assaying for depositable triglycerides in said one or more wood pulp samples, by reacting depositable triglycerides in a wood pulp sample in the presence of a lipolytic enzyme to form glycerol and fatty acids and comparing the amount of glycerol or fatty acids present in the wood pulp sample before treatment with the lipolytic enzyme with the amount of glycerol or fatty acids present in the wood pulp sample after treatment with the lipolytic enzyme; and (c) activating one or more pitch control measures as needed based on the results obtained in step (b).

58. A kit for pitch control in a pulp and paper mill comprising: a means for assaying for depositable triglycerides in a wood pulp sample obtained from one or more sample points in a pulp and paper mill, wherein the means for assaying utilizes the method of claim 1; and a device for applying one or more pitch control measures, wherein said device is in operable communication with said means for assaying, such that the device can be activated as needed in response to the depositable triglycerides assay.

59. The kit of claim 58, wherein the pitch control measures are activated automatically in response to the depositable triglycerides assay.

60. The kit of claim 58, wherein the means for assaying comprises an electrode assembly suitable for measuring the change in concentration of an electrochemical species, which change is produced by treating the wood pulp sample with a lipolytic enzyme.

* * * * *

UNITED STATES PATENT AND TRADEMARK OFFICE
CERTIFICATE OF CORRECTION

PATENT NO. : 7,067,244 B2
APPLICATION NO. : 10/126173
DATED : June 27, 2006
INVENTOR(S) : Chengliang Jiang et al.

It is certified that error appears in the above-identified patent and that said Letters Patent is hereby corrected as shown below:

Column 1, line 30, delete "of" and replace it with --by--.
Column 2, line 25, delete "residual" and replace it with --residue--.
Column 2, line 61, delete "depositions" replac it with --deposition--.
Column 3, line 16, delete "serves" and replace it with --serve--.
Column 4, line 4, delete "3,5-dichloro-2-hydoxybenene sulfonate" and replace it with --3,5-dichloro-2-hydroxybenzene sulfonate--.
Column 7, line 36, delete "aceyl" and replace it with --acyl--.
Column 8, lines 45-46, delete "3,5-dichloro-2-hydoxybenzene sulfonate" and replace with --3,5-dichloro-2-hydroxybenzene sulfonate--.
Column 8, lines 61-62, delete "3-(4',5'-dimethylthiazolyl-2)-2,4-diphenyltetetrazolium bromide" and replace it with
--3-(4',5'-dimethylthiazolyl-2)-2,4-diphenyltetrazolium bromide--.
Column 11, line 8, delete "in" and replace it with --on--.
Column 12, line 2, delete "dihyroxyacetone phosphate" and replace it with
--dihydroxyacetone phosphate--.
Column 12, lines 63-64, delete "3-(4',5'-dimethylthiazolyl-2)-2,4-diphenyltetatrazolium bromide" and replace it with --3-(4',5'-dimethylthiazolyl-2)-2,4,-diphenyltetrazolium bromide--.
Column 16, line 14, --a-- should be inserted before the word "device".
Column 17, line 25, delete the word "to".
Column 20, line 11, delete "dihyroxyacetone phosphate" and replace it with
--dihydroxyacetone phosphate--.
Column 27, line 33-34, delete "glycerol-l-phospate" and replace it with --glycerol-1-phosphate--.
Column 28, line 55, delete "glycerol-1-phospate" and replace it with --glycerol-1-phosphate--.
Claim 32, line 21, delete "dihyroxyacetone phosphate" and replace it with
--dihydroxyacetone phosphate--.
Column 15, line 55 delete "glycerol phospate oxidase" and replace it with --glycerol phosphate oxidase-- and delete "dihydoxyacetone phospate" and replace it with
--dihydroxyacetone phosphate--.
Claim 5, line 59, delete "lipolycic" and replace it with --lipolytic--.
Claim 41, line 61, delete "mensurable suedes" and replace it with --measurable species--.

UNITED STATES PATENT AND TRADEMARK OFFICE
CERTIFICATE OF CORRECTION

PATENT NO. : 7,067,244 B2
APPLICATION NO. : 10/126173
DATED : June 27, 2006
INVENTOR(S) : Chengliang, Jiang et al.

It is certified that error appears in the above-identified patent and that said Letters Patent is hereby corrected as shown below:

Claim 56, line 9, delete "tote" and replace it with --to the--.

Signed and Sealed this

Twenty-eighth Day of November, 2006

JON W. DUDAS
*Director of the United States Patent and Trademark Office*